United States Patent
Nho et al.

(10) Patent No.: US 11,541,096 B2
(45) Date of Patent: Jan. 3, 2023

(54) **COMPOSITION FOR WOUND TREATMENT CONTAINING EXTRACT OF *STELLERA CHAMAEJASME* OR FRACTION THEREOF AND METHOD FOR TREATING WOUND OF SUBJECT**

(71) Applicant: KOREA INSTITUTE OF SCIENCE AND TECHNOLOGY, Seoul (KR)

(72) Inventors: Chu Won Nho, Gangneung-si (KR); Myung Suk Kim, Gangneung-si (KR); Hee Ju Lee, Gangneung-si (KR); Kil Choo Moon, Seoul (KR); Sang Rok Oh, Seoul (KR); Dulamjav Batsuren, Ulaanbaatar (MN)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 419 days.

(21) Appl. No.: 15/566,472

(22) PCT Filed: Apr. 11, 2016

(86) PCT No.: PCT/KR2016/003754
§ 371 (c)(1),
(2) Date: Oct. 13, 2017

(87) PCT Pub. No.: WO2016/167518
PCT Pub. Date: Oct. 20, 2016

(65) Prior Publication Data
US 2018/0071355 A1    Mar. 15, 2018

(30) Foreign Application Priority Data

Apr. 13, 2015 (KR) .................... 10-2015-0052084
Feb. 19, 2016 (KR) .................... 10-2016-0019774
Feb. 25, 2016 (KR) .................... 10-2016-0022822
Mar. 30, 2016 (KR) .................... 10-2016-0038758

(51) Int. Cl.
| A61K 36/83 | (2006.01) |
| A61K 9/20 | (2006.01) |
| A61K 9/16 | (2006.01) |
| A61K 9/48 | (2006.01) |
| A61K 8/9789 | (2017.01) |
| A61K 8/96 | (2006.01) |
| A61Q 19/08 | (2006.01) |

(52) U.S. Cl.
CPC .............. *A61K 36/83* (2013.01); *A61K 8/96* (2013.01); *A61K 8/9789* (2017.08); *A61K 9/1623* (2013.01); *A61K 9/1652* (2013.01); *A61K 9/2009* (2013.01); *A61K 9/2018* (2013.01); *A61K 9/2059* (2013.01); *A61K 9/4858* (2013.01); *A61K 9/4875* (2013.01); *A61Q 19/08* (2013.01); *A61K 2236/00* (2013.01)

(58) Field of Classification Search
None
See application file for complete search history.

(56) References Cited

U.S. PATENT DOCUMENTS

| 5,616,609 A * | 4/1997 | Ikekawa .............. C07D 493/22 514/450 |
| 2005/0169947 A1* | 8/2005 | Korte .................... A61K 8/602 424/401 |

FOREIGN PATENT DOCUMENTS

| CN | 1410424 A |   | 4/2003 |
| CN | 1548423 A |   | 11/2004 |
| CN | 101607028 A | * | 12/2009 |
| CN | 101755850 A | * | 6/2010 |
| CN | 103638409 A |   | 3/2014 |
| CN | 103721117 A |   | 4/2014 |
| CN | 105418570 A |   | 3/2016 |
| JP | 2008-266156 A |   | 11/2008 |
| JP | 2011-102264 A |   | 5/2011 |
| JP | 2013-18726 A |   | 1/2013 |
| KR | 10-0872481 B1 |   | 12/2008 |
| KR | 2011027339 A | * | 3/2011 |
| KR | 10-1597762 B1 |   | 2/2016 |
| KR | 10-1679391 B1 |   | 12/2016 |

OTHER PUBLICATIONS

Li et al., Chemical Constituents and Pharmacological Activities of Stellera chamaejasme, .2018, Current Pharmaceutical Design, 24 : 1-14.*
Narantuya et al., 1994, Chemical Study of Plants of the Mongolian Flora. Coumarins of Stellera chamaejasme: The Structure of Chamaejasmoside—A New Bicoumarin Glycoside, Chemistry of Natural Compounds, vol. 30, No. 2 , pp. 197-199.*
Barnaulov, "Effect of Powders and Decoctions from Some Plants of the Flora of Mongolia on Wound Healing in Mice," Rastitel'nye Resursy. (1981), vol. 17, No. 3, pp. 462-469 (abstract).
Office Action dated Nov. 13, 2018, in Japanese Patent Application No. 2018-062070.
Wang et al., "Accumulation of Flavonoids and Antioxidant Activity of *Stellera chamaejasme* by Efficient Callus Culture," Hort. Environ. Biotechnol. (2013), vol. 54, No. 5, pp. 441-449.
International Search Report for PCT/KR2016/003754 (PCT/ISA/210) dated Sep. 27, 2016.
Murugananthan et al., "Immunomodulatory Constituents from Plant Origins: A Review of Isolated Biomolecules", International Journal of Pharmaceutical Sciences and Research, 2013, vol. 4, pp. 2459-2469.

(Continued)

*Primary Examiner* — Terry A McKelvey
*Assistant Examiner* — Catheryne Chen
(74) *Attorney, Agent, or Firm* — Birch, Stewart, Kolasch & Birch, LLP

(57) ABSTRACT

Provided are a composition including *Stellera chamaejasme* extract for treating wound, a method of treating wound of a subject, a cosmetic composition for wound improving, skin wrinkle improving, or skin anti-aging, and a method of cosmeticizing for wound improving, skin wrinkle improving, or skin anti-aging.

4 Claims, 15 Drawing Sheets

Specification includes a Sequence Listing.

(56) References Cited

OTHER PUBLICATIONS

Office Action dated May 12, 2017 of Korean Patent Application No. 10-2016-0038758.
Written Opinion of the International Searching Authority for PCT/KR2016/003754 (PCT/ISA/237) dated Sep. 27, 2016.
Yang et al., "Antimitotic and Antifungal C-3/C-3"-Biflavanones from Stellera chamaejasme", Chemical and Pharmaceutical Bulletin, 2005, vol. 53, pp. 776-779.
Database Biosis [Online], Biosciences Information Service, Philadelphia, PA, US: Jan. 1, 1981; Barnaulov, O.D., "Effects of Powders and Decoctions from Some Plants of the Flora of Mongolia on Wound Healing in Mice Study," Database accession No. PREV198375059574.
Extended European Search Report dated Jan. 12, 2018, in European Patent Application No. 17201805.3.
Tsolmon et al., "Inhibition of cell growth by Stellera chamaejasme extract is associated with induction of autophagy and differentiation in chronic leukemia K562 cells," Journal of Bioscience and Bioengineering (2010), vol. 110, No. 2, pp. 262-268.
Office Action dated Apr. 20, 2020, in Korean Patent Application No. 201680026656.8.
Wan et al., "Inhibitory effects of Stellera chamaejasme L. extraction on hypertrophic scar-derived fibroblasts," Clin. Pharm. J. (Jul. 2005), vol. 40, No. 13, pp. 986-987 (with English abstract).
Zheng et al., "Changes of Flavonoids Content in Stellara chamaejasme in Songnen Grassland of Heilongjiang Province," Journal of Northeast Forestry University (2006), vol. 34, No. 4, pp. 59-60, with English abstract.
Office Action dated Dec. 29, 2020, in Chinese Patent Application No. 201680026656.8.
Zhu Yin-long, Practical Clinical Pharmacy ofthe Traditional Chinese Medicine, Shaanxi Science and Technology Press, the first edition, Jul. 31, 2013, p. 151-152.

\* cited by examiner

| NORMAL | VEHICLE | STELLERA | CENTELLA |
| (G1) | (G2) | CHAMAEJASME | ASIATICA |
|  |  | (G3) | (G4) |

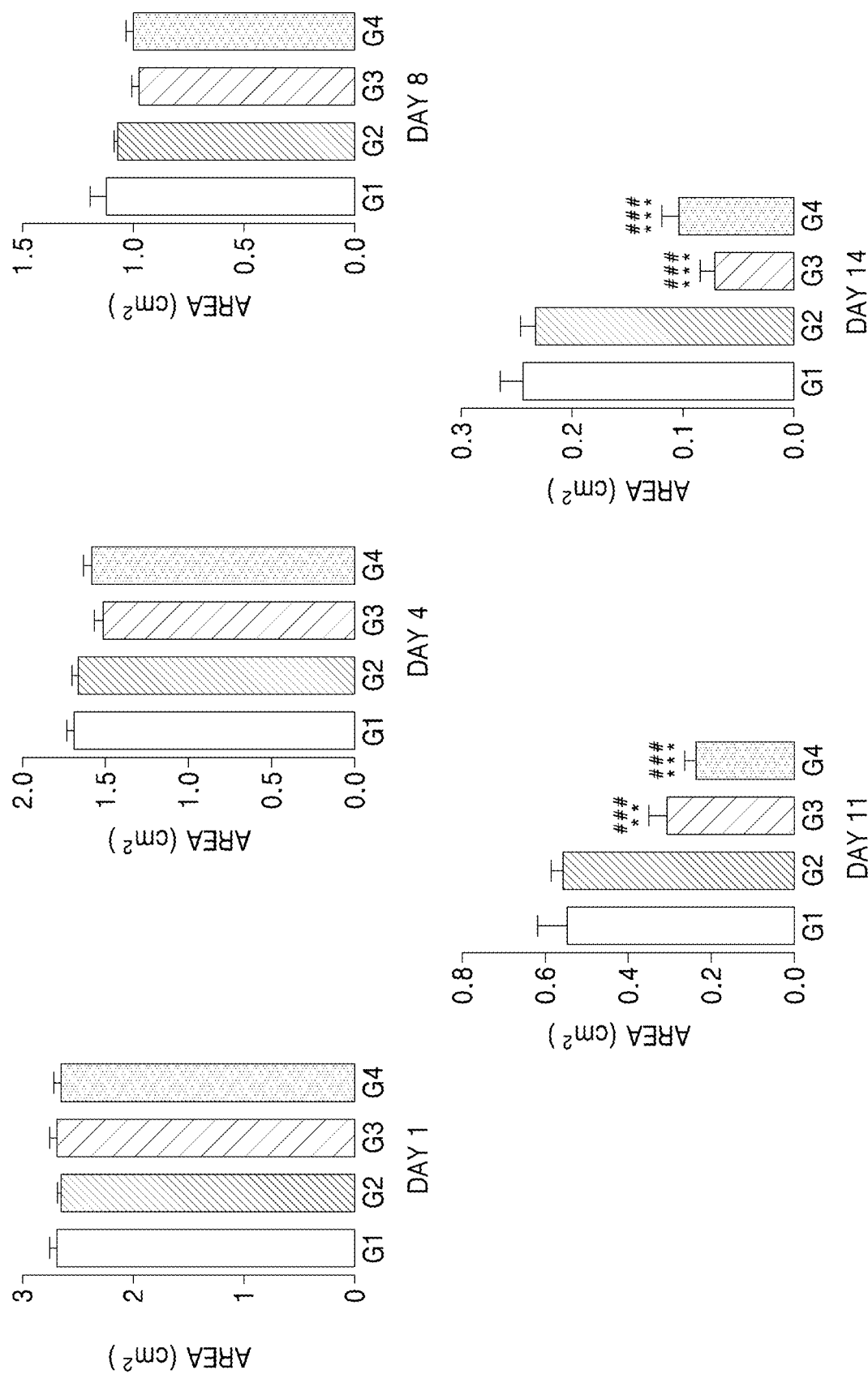

COMPOSITION FOR WOUND TREATMENT CONTAINING EXTRACT OF *STELLERA CHAMAEJASME* OR FRACTION THEREOF AND METHOD FOR TREATING WOUND OF SUBJECT

TECHNICAL FIELD

The present invention relates to a composition including *Stellera chamaejasme* extract or a fraction thereof for treating wound, a method of treating wound of a subject including administering a therapeutically effective amount of the composition to a subject to treat the wound, a cosmetic composition for wound improving, skin wrinkle improving, or skin anti-aging, and a method of cosmeticizing for wound improving, skin wrinkle improving, or skin anti-aging.

BACKGROUND ART

The skin acts as a shield to protect a body from the outside. When a wound is formed in skin, the wounded part is filled with blood by natural healing action of a living body. As the number of granules of platelet is reduced, and the activation of Hageman factor starts, wound healing proceeds. Coagulation of blood is a temporary defensive action that protects exposed wounded tissues and provides a basis for cells to move during the wound healing.

Wound treatment and/or healing occurs in three major stages. The first stage is an inflammatory phase characterized by inflammation in the wounded part. Inflammation may be generally short-lived, when no serious infection occurs. The second stage is a proliferative phase, which is characterized by epithelialization, angiogenesis, granulation tissue formation, and collagen deposition. Angiogenesis accompanied with new capillary formation is to deliver nutrients and maintain granulation tissue formation. Without the formation of new capillaries into the wound, essential nutrients may not reach the wound, forming a wound that is not chronically healed. The surface of the injured wound is covered by a layer of keratinocytes, resulting in a new epidermis and a re-epithelialization in which an epithelium layer is reconstructed. Once re-epithelialization is complete, a series of processes are performed in which the wounded area is reduced through an increase in and reorganization of connective tissues. The final stage of wound healing is a maturational phase in which fibroblasts differentiate into collagen. During the maturational phase, a clot of cells and capillaries of convalescent tissues gradually disappear, and scars may be formed if the cells and capillaries of these tissues are hyperplastic or not normally degraded.

Since it is important not only to treat wounds quickly during wound healing, but also to treat them without side effects or scars, efforts to find such materials have been continued.

DETAILED DESCRIPTION OF THE INVENTION

Technical Problem

According to an aspect, a composition for treating a wound includes *Stellera chamaejasme* extract or a fraction thereof as an active ingredient.

According to another aspect, a method of treating a wound of a subject includes administering a therapeutically effective amount of the composition to a subject to treat the wound.

According to another aspect, a cosmetic composition for wound improving, skin wrinkle improving, or skin anti-aging includes a *Stellera chamaejasme* extract or a fraction thereof as an active ingredient.

According to another aspect, a method of cosmeticizing for wound improving, skin wrinkle improving, or skin anti-aging includes applying the cosmetic composition to a subject.

Technical Solution

According to an aspect, a composition for treating wound includes a *Stellera chamaejasme* extract or a fraction thereof as an active ingredient, wherein the *Stellera chamaejasme* extract is extracted from an aerial part of *Stellera chamaejasme*.

The *Stellera chamaejasme* extract is an extract extracted from, using a solvent, the whole, part of, or a material derived from an aerial part of *Stellera chamaejasme*. The part of *Stellera chamaejasme* may be stem, leaf, flower, or petal of *Stellera chamaejasme*. *Stellera chamaejasme* may be grown in mountainous areas of Mongolia. The mountainous areas may be near Ulaanbaatar. *Stellera chamaejasme* may grow to a height of about 30 centimeters (cm) to 40 cm. A length of a leaf of *Stellera chamaejasme* may be about 15 millimeters (mm) to 27 mm, and the leaf may be lanceolate. A surface of the leaf may be green and a backside thereof may be bluish gray. Both sides of the leaf have no hairs and a petiole is short. The whole, part of, or a material derived from an aerial part of *Stellera chamaejasme* used in extraction may be ground, sliced, or suitably dried.

The solvent may be water, acetone, an alcohol such as a $C_1$-$C_6$ alcohol, or a mixture thereof. The $C_1$-$C_6$ alcohol may be methanol, ethanol, propanol, isopropanol, 1,3-propanediol, butanol, pentanol, hexanol and the like. The solvent may be, for example, a mixture of water and alcohol, that is, an aqueous alcohol solution. A concentration of alcohol of the aqueous solution of alcohol may be in a range of 1% (v/v) to 100% (v/v), for example, 1% (v/v) to 99.5% (v/v), 10% (v/v) to 100% (v/v), 20% (v/v) to 100% (v/v), 30% (v/v) to 100% (v/v), 40% (v/v) to 100% (v/v), 50% (v/v) to 100% (v/v), 60% (v/v) to 100% (v/v), 70% (v/v) to 100% (v/v), or 75% (v/v) to 100% (v/v). The aqueous solution of alcohol may be an aqueous solution of methanol, ethanol, or butanol. The acetone may have a concentration of 100%.

The extraction may include adding the extraction solvent to the whole, part of, or a material derived from an aerial part of *Stellera chamaejasme*. The amount of solvent may be 3 litres (L) to 10 L, for example, 3 L to 7 L, 3 L to 5 L, 5 L to 10 L, or 4 L to 10 L per 1 kilogram (kg) of the whole, part of, or a material. For example, the extraction may include adding 3 L to 10 L of the extraction solvent to 1 kg of the whole, part of, or a material derived from an aerial part of *Stellera chamaejasme*.

The extraction may be performed by warmed liquid extraction, pressurized liquid extraction (PLE), microwave assisted extraction (MAE), subcritical extraction (SE), or a combination thereof. The SE may be subcritical water extraction (SWE). The SWE is also referred to as superheated water extraction or pressurized hot water extraction (PHWE). The warmed liquid extraction may be reflux extraction.

The extraction may be performed at a temperature in a range of 4° C. to 70° C., for example, 4° C. to 50° C., 4° C. to 40° C., 4° C. to 30° C., 10° C. to 70° C., 15° C. to 70° C., 20° C. to 70° C., 4° C. to 50° C., 10° C. to 50° C., 4° C. to 40° C., 4° C. to 30° C., 10° C. to 40° C., 10° C. to 35° C., or 10° C. to 30° C. A duration of the extraction, which may vary depending on a temperature, may be for 1 hour to 2 months, for example, 1 hour to 1 month, 1 hour to 15 days, 1 hour to 10 days, 1 hour to 5 days, 1 hour to 3 days, 1 hour to 2 days, 1 hour to 1 day, 5 hours to 1 month, 5 hours to 15 days, 5 hours to 10 days, 5 hours to 5 days, 5 hours to 3 days, 5 hours to 2 days, 5 hours to 1 day, 10 hours to 1 month, 10 hours to 15 days, 10 hours to 10 days, 10 hours to 5 days, 10 hours to 3 days, or 10 hours to 2 days. The extraction may include mixing the whole, part of, or a material derived from an aerial part of Stellera chamaejasme with the solvent and allowing the mixture to stand for a certain period of time. The allowing the mixture to stand may include suitably stirring. The extraction may be repeated one or more times, for example, one to five times.

The extraction may be carried out by a known method such as filtration for the mixture to isolate an extract and remove plant residues. The extraction may also include removing a solvent from a resulting extract by a known method such as concentration under reduced pressure. The extraction may also include preparing a dried extract by drying, such as lyophilization, of a resulting extract.

With regard to the composition, the term "fraction" refers to a material, in which the Stellera chamaejasme extract is fragmented into a part of its components, i.e., a fractioned material. The fraction may be obtained by solvent fractionation. The fractionation may be mixing Stellera chamaejasme extract with a solvent and separating a material present in the solvent. The fraction may be a hexane fraction; an ethyl acetate fraction; a butanol fraction; or a water fraction, wherein the hexane fraction, the ethyl acetate fraction, the butanol fraction, and the water fraction are obtained by suspending Stellera chamaejasme extract in water and then subsequently fractionating a resulting suspension by using hexane, ethyl acetate, and butanol.

In detail, Stellera chamaejasme extract may be mixed with water, this mixture may be mixed with hexane, and after allowing the resulting mixture for a certain period of time, a hexane layer may be separated, from which a fraction may be separated. Thereby, the hexane fraction may be obtained. Separation of hexane fraction may include removing hexane from a hexane layer. A water layer, remaining after the separating the hexane fraction, may be mixed with ethyl acetate, and after allowing the resulting mixture for a certain period of time, an ethyl acetate layer may be separated, from which a fraction may be separated. Thereby, the ethyl acetate fraction may be obtained. Separation of ethyl acetate fraction may include removing ethyl acetate from an ethyl acetate layer. A water layer, remaining after the separating the ethyl acetate fraction, may be mixed with butanol, and after allowing the resulting mixture for a certain period of time, a butanol layer may be separated, from which a fraction may be separated. Thereby, the butanol fraction may be obtained. Separation of butanol fraction may include removing butanol from a butanol layer. Conditions for the fractionation, such as temperature conditions, pressure conditions, time, amount or concentration of a solvent used, stirring, and the like, may be the same as those described above with regard to preparation of the Stellera chamaejasme extract. The fractionation may be repeated one or more times, for example, one to five times. A sequence of the fractionation is for illustrative purpose only; and thus fractionation using hexane, ethyl acetone, and butanol may be performed in any sequence.

Separation of the fraction may be performed by a known method such as filtration. The fractionation may also include removing a solvent from a resulting fraction by a known method such as concentration under reduced pressure. The fractionation may also include concentrating and/or drying the resulting fraction. The concentrating may be concentrating under reduced pressure. The drying may include drying under reduced pressure, boiling drying, spray drying, drying at room temperature, or freeze drying.

With regard to the composition, the term "wound" refers to an injury formed on the body when a tissue is cut, torn, broken, burned, or traumatized, or caused by a damage or disease causing such injury. The term "tissue" refers to an organized collection of cells specialized to perform a particular function. Tissues may include eyes, mucus, lung, kidney, heart, viscera, tendons, vascular tissues, bones, skin, connective tissues, and nerves such as spinal cord. The wound may be an open wound where surface is cracked open or a closed wound where surface is not open. An example of the wound may be an open wound in skin. The wound may include lesion, sore, necrosis, and ulcer. The necrosis may be relevant to a dead tissue resulting from infection, damage or infarction. The ulcer may be a local defect or exfoliation of a surface of an organ or tissue resulting from dissection of a necrotic tissue.

An example of the wound may be a wound of injury in epidermis; dermis; epidermis and dermis; or epidermis, dermis and subcutaneous fat layer of skin.

Examples of the wound may include cut, incisions (e.g., surgical incisions), abrasions, lacerations, fracture, contusions, burns, or amputations.

The term "treatment" as used herein may be providing for wound healing at a shortened time, as compared with natural healing. The treatment may include improvement and/or alleviation of wound. The treatment may also include all treatments for wound and/or wound related diseases. The treatment may refer to healing and/or regeneration of a damaged tissue caused by wound. The wound treatment may include a meaning of skin regeneration. The treatment may also maintain an original composition of the damaged tissue. In addition, the treatment may promote healing and/or regeneration of the damaged tissue while minimizing complications and/or scars of wound related diseases.

The composition may be for promoting whole stages of a wound healing process. Also, the composition may promote a proliferative and/or maturation phase of a wound healing process. Thus, the composition may be for treating would in a proliferative and/or maturation phase.

The composition may include Stellera chamaejasme extract or a fraction thereof in a range of 0.001 percent by weight (wt %) to 80 wt %, for example, 0.01 wt % to 60 wt %, 0.01 wt % to 40 wt %, 0.01 wt % to 30 wt %, 0.01 wt % to 20 wt %, 0.01 wt % to 10 wt %, 0.01 wt % to 5 wt %, 0.05 wt % to 60 wt %, 0.05 wt % to 40 wt %, 0.05 wt % to 30 wt %, 0.05 wt % to 20 wt %, 0.05 wt % to 10 wt %, 0.05 wt % to 5 wt %, 0.1 wt % to 60 wt %, 0.1 wt % to 40 wt %, 0.1 wt % to 30 wt %, 0.1 wt % to 20 wt %, 0.1 wt % to 10 wt %, or 0.1 wt % to 5 wt %, based on the total amount of the composition.

The composition may be a pharmaceutical composition. The composition may further include a pharmaceutically acceptable diluent or carrier. The diluent may be lactose, corn starch, soybean oil, microcrystalline cellulose, or mannitol. A lubricant may be magnesium stearate, talc, or a combination thereof. The carrier may be an excipient, a disintegrant, a binder, a lubricant, or a combination thereof. The excipient may be microcrystalline cellulose, lactose, low-substituted hydroxy cellulose, or a combination thereof. The disintegrant may be carboxymethylcellulose calcium, sodium starch glycolate, anhydrous calcium monohydrogen phosphate, or a combination thereof. The binder may be polyvinylpyrrolidone, low-substituted hydroxypropyl cellulose, hydroxypropyl cellulose, or a combination thereof. The lubricant may be magnesium stearate, silicon dioxide, talc, or a combination thereof.

The composition may be formulated into a parenteral dosage form. The parenteral dosage form may be an injection or an external preparation for skin. The external preparation for skin may be a cream, a gel, an ointment, a skin emulsifier, a skin suspension, a transdermal patch, a drug-containing bandage, lotion, or a combination thereof.

According to a need, the external preparation for skin may be appropriately compounded with a component generally used in external skin preparations, such as cosmetics or medicines, e.g., an aqueous component, an oily component, a powder component, alcohols, a moisturizer, a thickener, an ultraviolet absorber, a whitening agent, an antiseptic agent, an antioxidant, a surfactant, a perfume, a coloring agent, various skin nutrients, or a combination thereof.

According to a need, the external preparation for skin may be appropriately compounded with a metal sequestering agent such as disodium edetate, trisodium edetate, sodium citrate, sodium polyphosphate, sodium metaphosphate, or gluconic acid; drugs such as caffeine, tannin, verapamil, licorice extract, glabridin, hot water extract of fruit, various herbal medicines, tocopherol acetate, glycyrrhizic acid, or tranexamic acid and a derivative or salt thereof; vitamin C; magnesium ascorbyl phosphate; ascorbic acid glucoside; albutin; kojic acid; or sugars such as glucose, fructose, mannose, sucrose, or trehalose.

The composition may be for promoting expression of collagen gene in a cell. The composition may increase expression of collagen gene, or may increase activity of the collagen formed by the composition. The composition may also increase activity or expression of an up-stream enzyme or protein that produces collagen. In one embodiment, the composition may increase expression and/or activity of collagen so as to treat a wound. The composition may be used to increase expression and/or activity of collagen so as to maintain or increase elasticity of a tissue that contains collagen. For example, the composition may maintain or promote elasticity of skin so as to reduce formation of wrinkles in tissue and remove wrinkles, where the tissue contains collagen. The collagen may be Type I collagen or Type III collagen. The gene encoding the collagen may be selected from the group consisting of COL1A1 and COL3A1.

The composition may increase production of a differentiation factor for keratinocyte. The composition may, for example, promote expression of a differentiation factor gene of keratinocyte. The differentiation factor may be filaggrin (FLG), loricrin (LOR), or involucrin (IVL). The composition may promote migration of keratinocyte to wound.

The composition may increase expression of collagen gene, or may increase activity of collagen formed by the composition. The composition may also increase activity or expression of an up-stream enzyme or protein that produces collagen.

According to another aspect, a method of treating a wound of a subject includes administering a therapeutically effective amount of the composition to a subject to treat the wound. The composition is the same as described above.

The administration may be carried out using a method that is known to those skilled in the art. The administration, for example, may be carried out by using any route that allows a direct administration to a subject, such as an intravenous administration, an intramuscular administration, a transdermal administration, a mucosal administration, an intranasal administration, an intratracheal administration, or a subcutaneous administration. The administration may be a systemic or topical administration. The administration may be a topical administration to a wounded part.

The subject may be a mammal, e.g., humans, cattle, horses, pigs, dogs, sheep, goats, or cats. The subject may have a wound. The wound may be a skin wound.

The administration may be administration of *Stellera chamaejasme* extract to a subject at an amount in a range of 0.1 milligrams (mg) to 1,000 mg, for example, 0.1 mg to 500 mg, 0.1 mg to 100 mg, 0.1 mg to 50 mg, 0.1 mg to 25 mg, 0.1 mg to 5 mg, 1 mg to 1,000 mg, 1 mg to 500 mg, 1 mg to 100 mg, 1 mg to 50 mg, 1 mg to 25 mg, 5 mg to 1,000 mg, 5 mg to 500 mg, 5 mg to 100 mg, 5 mg to 50 mg, 1 mg to 5 mg, 5 mg to 25 mg, 10 mg to 1,000 mg, 10 mg to 500 mg, 10 mg to 100 mg, 10 mg to 50 mg, or 10 mg to 25 mg.

According to another aspect, a cosmetic composition for wound improving, skin wrinkle improving, or skin anti-aging includes a *Stellera chamaejasme* extract or a fraction thereof as an active ingredient. The *Stellera chamaejasme* extract is the same as described above.

The term "for wound improving" may be construed as including a use for lowering or alleviating a degree of wound. For example, the wound improving may refer to lower or alleviate a degree of formed wound. The term "skin wrinkle improving" may be construed as including maintaining elasticity of skin so as to prevent wrinkle formation or remove formed wrinkles.

The extract promotes production of collagen in fibroblasts. Collagen is a major component of a dermal layer of skin and is an elastic protein with strong binding properties to moisture. That is, collagen has a property of imparting elasticity to skin and has an effect of preventing wrinkle formation. As a human grows older, an amount of collagen in skin decreases, and the skin undergoes aging process that causes the skin to lose elasticity and to form wrinkles. Thus, the composition of the claimed invention including the extract may be used as a cosmetic composition for skin wrinkle improving or skin anti-aging. The cosmetic composition may not contain any other active ingredient having a wrinkle improving or anti-aging effect other than the extract.

The cosmetic composition may be provided in any formulation suitable for topical application. For example, the cosmetic composition may be provided as a formulation of a solution, an emulsion obtained by dispersing an oil phase in an aqueous phase, an emulsion obtained by dispersing an aqueous phase in an oil phase, a suspension, a solid, a gel, a powder, a paste, a mask pack, a sheet, a foam, or an aerosol composition. Compositions of such formulations may be prepared according to conventional methods in the art.

The cosmetic composition may further include a moisturizer, an emollient agent, an ultraviolet absorber, an antiseptic agent, a germicide, an antioxidant, a pH adjusting agent, organic and inorganic pigments, a perfume, or a cooling agent, an antiperspirant. An amount of an additional component such as the moisturizer may be easily selected by one of ordinary skilled in the art within a range not to impair the purpose and effect of the present invention, and the amount thereof may be in a range of 0.01 wt % to 5 wt %, specifically, 0.01 wt % to 3 wt %.

The composition may include *Stellera chamaejasme* extract or a fraction thereof in a range of 0.001 wt % to 80 wt %, for example, 0.01 wt % to 60 wt %, 0.01 wt % to 40 wt %, 0.01 wt % to 30 wt %, 0.01 wt % to 20 wt %, 0.01 wt % to 10 wt %, 0.01 wt % to 5 wt %, 0.05 wt % to 60 wt %, 0.05 wt % to 40 wt %, 0.05 wt % to 30 wt %, 0.05 wt % to 20 wt %, 0.05 wt % to 10 wt %, 0.05 wt % to 5 wt %, 0.1 wt % to 60 wt %, 0.1 wt % to 40 wt %, 0.1 wt % to 30 wt %, 0.1 wt % to 20 wt %, 0.1 wt % to 10 wt %, or 0.1 wt % to 5 wt %, based on the total amount of the composition.

According to another aspect, a method of cosmeticizing skin for wound improving, skin wrinkle improving, or skin anti-aging includes applying the cosmetic composition to a subject.

The method may be for wound improving, skin wrinkle improving, or skin anti-aging.

In the method, the cosmetic composition is applied to a number of treatments, particularly cosmetic treatments, of skin, including the scalp, lips, and hairs.

In the method, the stage of applying to skin include contacting the composition with the skin to allow components of the composition to permeate into the skin. The stage of applying to skin may be combined with any other means such as electrical or magnetic forces, e.g., iontophoresis, so as to help the composition permeate into the skin.

Advantageous Effects of the Invention

When a composition for treating a wound, according to an aspect, is used, the wound of a subject may be efficiently treated.

When a method of treating a wound of a subject, according to an aspect, is used, the wound of a subject may be efficiently treated.

When a cosmetic composition for wound improving, skin wrinkle improving, or skin anti-aging, according to an aspect, is used, wound improving, skin wrinkle improving, or skin anti-aging may become effective.

When a method of cosmeticizing skin, according to an aspect, is used, wound improving, skin wrinkle improving, or skin anti-aging may be achieved.

DESCRIPTION OF THE DRAWINGS

FIG. 16 shows quantitative test results where a stem extract of *Stellera chamaejasme* promotes recovery of a rift wound in an animal experiment.

BEST MODE

Figure 1:
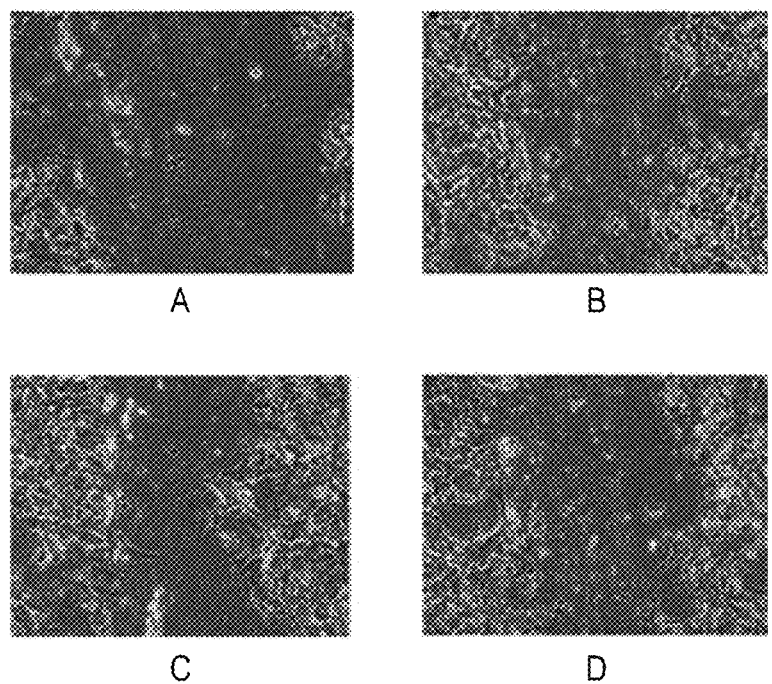
FIG. 1 shows that an ethanol extract of an aerial part of *Stellera chamaejasme* promotes migration of keratinocyte.

Hereinafter, the present invention will be described in more detail with reference to Examples. However, these Examples are for illustrative purposes only, and the present invention is not intended to be limited by these Examples.

Example 1: Preparation of *Stellera chamaejasme* Extract and Fraction Thereof

In Example 1, a *Stellera chamaejasme* extract was prepared from *Stellera chamaejasme*, and effects of the *Stellera chamaejasme* extract and a fraction thereof on wound treatment were tested.

1. Preparation of *Stellera chamaejasme* Extract and Fraction Thereof (1) Preparation of Ethanol Extract of *Stellera chamaejasme*

Only an aerial part of *Stellera chamaejasme* grown in Ulaanbaatar, Mongolia was collected. The collected aerial part was washed with water and dried. The dried aerial part of *Stellera chamaejasme* was sliced into, by using a straw cutter, small segments having a size in a range of 2 cm to 3 cm. 100 g of the sliced aerial part of *Stellera chamaejasme* and IL of 95% (v/v) aqueous solution of ethanol were added to a glass Erlenmeyer flask, and then mixed together. The mixture was extracted while stirring at a rate of 150 revolutions per minute (rpm) at a room temperature of about 20° C. for 48 hours.

Next, the mixture was filtered through a filter paper (Whatman, NO. 2, 8 micrometers (μm)) to thereby obtain a filtrate. The obtained filtrate was concentrated under reduced pressure by using a rotary evaporator (N-1100 available from EYELA). In order to remove the remaining solvent, freeze drying was performed thereon using a freeze dryer (FDCF-12003 available from Operon) for 48 hours, thereby obtaining 3 g of dried *Stellera chamaejasme* extract from which the solvent was removed.

(2) Preparation of Fraction of Ethanol Extract of *Stellera chamaejasme*

(2.1) Fraction of Ethanol Extract 3 g of the dried ethanol extract of *Stellera chamaejasme* and 100 mL of water were added to an Erlenmeyer flask and then suspended. The suspension was poured into 250 mL of a separatory funnel, and 100 mL of n-hexane (extra pure grade, 100% (v/v)) was added thereto, followed by sufficient shaking. Then, the mixture was allowed to stand for 3 hours at room temperature. A hexane layer was only taken from the mixture using a separatory funnel. This process was repeated for three times, and the obtained hexane layer was concentrated under reduced pressure by using a rotary evaporator (N-1100 available from EYELA) to thereby obtain a hexane fraction.

Also, in the same manner, 100% (v/v) of ethyl acetate was added to and mixed with the remaining water layer resulting from the hexane fraction separation process. Then, the same process was performed thereon to thereby obtain an ethyl acetate fraction.

Also, in the same manner, water-saturated butanol was added to and mixed with the remaining water layer resulting from the ethyl acetate fraction separation process. Then, the same process was performed thereon to thereby obtain a butanol fraction. The remaining part of was used a water fraction The ethanol extract of *Stellera chamaejasme* and a fraction thereof were dissolved in dimethyl sulfoxide (DMSO) at a concentration of 20 milligrams per milliliters (mg/mL) and used in the following experiment.

(2.2) Extracts of Other Solvents and Fraction Thereof

Extracts of other solvents and fractions thereof were obtained in substantially the same manner as in Section (2.1), except that, 100% (v/v) acetone, methanol at a given concentration, butanol were used instead of ethanol.

2. Increase of Migration of Human Keratinocyte

It was tested whether the extract of *Stellera chamaejasme* or a fraction thereof increases migration of a human keratinocyte as follows.

HaCaT human keratinocytes were added to each well of a 24-well microtiter plate containing 1 mL of HyClone Dulbecco's modified eagle's medium (DMEM) containing 2.5% (v/v) of fetal bovine serum such that $2\times10^5$ cells were placed in each well. Next, the keratinocytes were cultured at a temperature of 37° C. and in 5% $CO_2$ incubator until a confluency thereof reached 80%. A cell monolayer in the medium was "scratch-injured" with a p10 pipette tip.

Subsequently, 200 µl of serum-free DMEM, and the *Stellera chamaejasme* extract or a fraction thereof were added to the scratched cell monolayer at a concentration of 5 µg/mL and 10 µg/mL in each medium. Then, the human keratinocytes were cultured under the same culture conditions for 24 hours. In a negative control, the same amount of DMSO, which was used to dissolve the extract, was treated, and in a positive control, a *Centella asiatica* extract (10 µg/mL) was used at a given concentration. Thereafter, the cell layer was stained using a crystal violet reagent, to test a degree of recovery of scratch wound. The *Centella asiatica* extract was purchased from Biospectrum (Korea).

Figure 2:
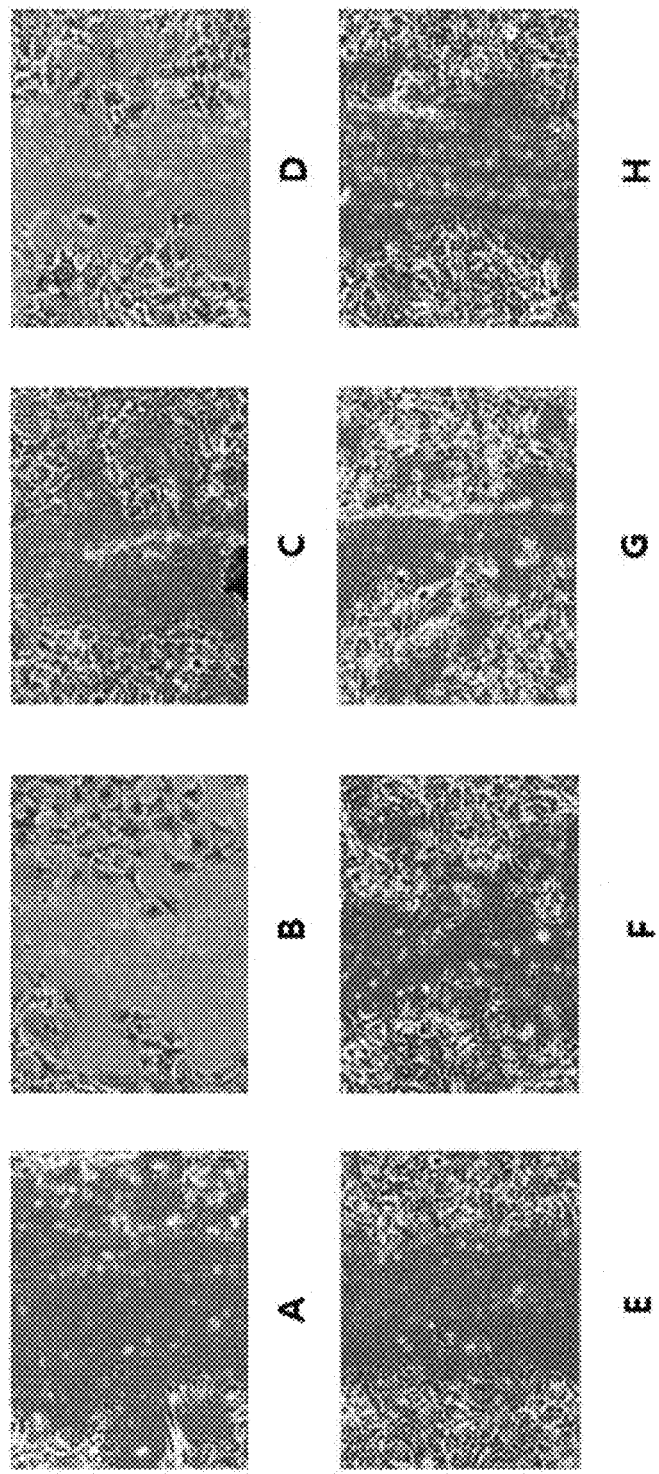
FIG. 2 shows that a fraction of an ethanol extract of an aerial part of *Stellera chamaejasme* promotes migration of keratinocyte.

FIG. 1 shows that the ethanol extract of an aerial part of *Stellera chamaejasme* promotes migration of keratinocyte. FIG. 2 shows that the fraction of an ethanol extract of an aerial part of *Stellera chamaejasme* promotes migration of keratinocyte. In FIGS. 1, A, B, C, and D respectively represent DMSO (negative control), the 5 µg/mL *Stellera chamaejasme* extract, the 10 µg/mL *Stellera chamaejasme* extract, and 10 µg/mL *Centella asiatica* extract (positive control). In FIGS. 2, A, B, C, D, E, F, G, and H respectively represent DMSO (negative control), the hexane fraction of the 5 µg/mL ethanol extract of an aerial part of *Stellera chamaejasme*, the ethyl acetate fraction of the 5 µg/mL ethanol extract of an aerial part of *Stellera chamaejasme*, the butanol fraction of the 5 µg/mL ethanol extract of an aerial part of *Stellera chamaejasme*, the 5 µg/mL *Centella asiatica* extract, the hexane fraction of the 10 µg/mL ethanol extract of an aerial part of *Stellera chamaejasme*, the ethyl acetate fraction of the 10 µg/mL ethanol extract of an aerial part of *Stellera chamaejasme*, and the butanol fraction of the 10 µg/mL ethanol extract of an aerial part of *Stellera chamaejasme*.

As shown in FIGS. 1 and 2, in the negative control conditions, the scratch injury of the treated cells remains relatively unhealed after 24 hours of the treatment. On the other hand, in the cells treated with the ethanol extract of an aerial part of *Stellera chamaejasme*, the scratch injury were healed due to proliferation and migration of wound edges, and thus after 24 hours, the scratched area reduced.

3. Increase of Expression of COL1A1 and COL3A1 Genes in Fibroblast

It was tested whether the *Stellera chamaejasme* extract promotes expression of collagen genes in a human fibroblast.

Human dermal fibroblasts (HDF, available from American Type Culture Collection, USA) were added to each well of a 6-well microtiter plate containing 2 mL of HyClone DMEM containing 2.5% (v/v) of fetal bovine serum such that $2\times10^6$ cells were placed in each well. Next, the human dermal fibroblasts were cultured under the same conditions until a confluency thereof reached 80%.

The *Stellera chamaejasme* extract was added to the cultured cells as such at a concentration of 1 µg/mL, 5 µg/mL, and 10 µg/mL in each medium. Then, the cell culture was allowed to continue for 24 hours under the same conditions described above. In a negative control, the same amount of DMSO, which was used to dissolve the extract, was treated, and in a positive control, a *Centella asiatica* extract (available from Biospectrum, Korea) was used. After a lapse of 24 hours, expression of collagen genes was tested by reverse transcription polymerase chain reaction (RT-PCR) assay. In detail, after a lapse of 24 hours, the total RNAs were collected from the cells using a TRIzol reagent (available from Invitrogen, Carlsbad, Calif., USA), which was then reverse transcripted to perform RT-PCR as follows. First, in order to synthesize cDNAs, the RNAs were reverse transcripted using a reverse transcriptase. The RT-PCR was performed using specific primers shown below. The relative amount of mRNA expression of each gene was standardized based on an amount of β-actin.

Figure 3:
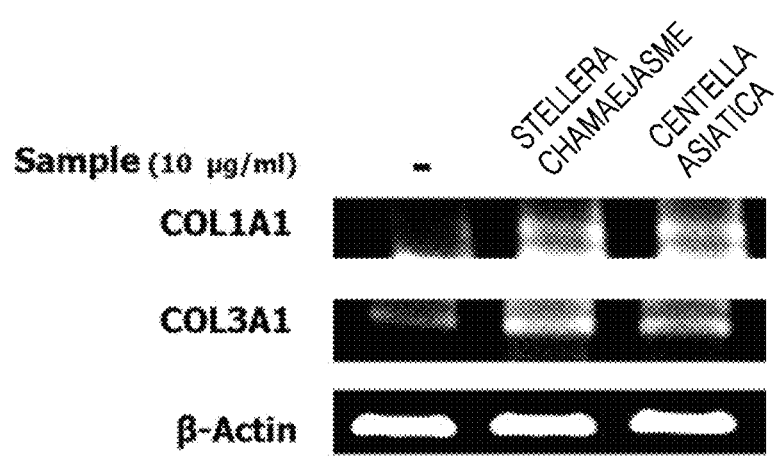
FIG. 3 shows that an ethanol extract of an aerial part of *Stellera chamaejasme* promotes expression of COL1A1 and COL3A1 genes in a fibroblast.

FIG. 3 shows that the ethanol extract of an aerial part of *Stellera chamaejasme* promotes expression of COL1A1 and COL3A1 genes in a fibroblast.

As shown in FIG. 3, it was found that the ethanol extract of an aerial part of *Stellera chamaejasme* significantly activates expression of at least one gene selected from the group consisting of COL1A1 and COL3A1, which are collagen synthesis-related factors.

Figure 4:
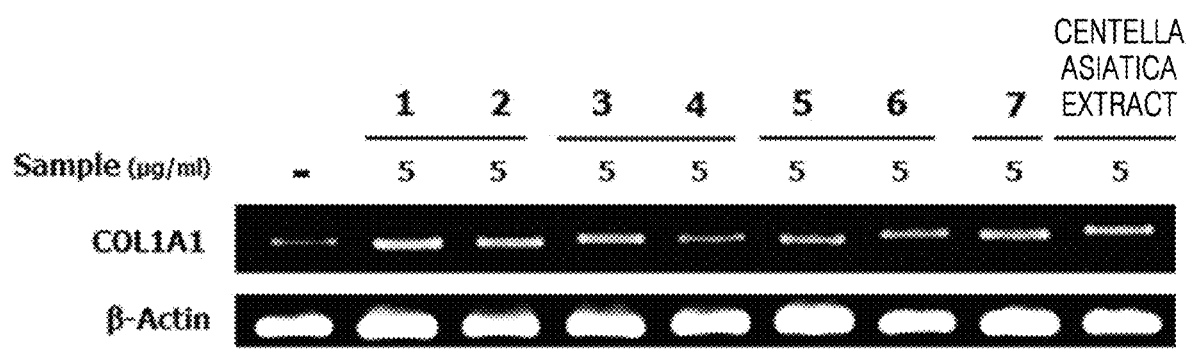
FIG. 4 shows that various solvent extracts of an aerial part of *Stellera chamaejasme* promote expression of COL1A1 and COL3A1 genes in a fibroblast.

FIG. 4 shows that various solvent extracts of an aerial part of *Stellera chamaejasme* promote expression of COL1A1 and COL3A1 genes in a fibroblast. In FIG. 4, Samples 1, 2, 3, 4, 5, 6, and 7 respectively represent an acetone extract, an acetone extract, a 100% ethanol extract, a 25% methanol extract, a 50% methanol extract, a 75% methanol extract, and a 100% methanol extract.

Figure 5:
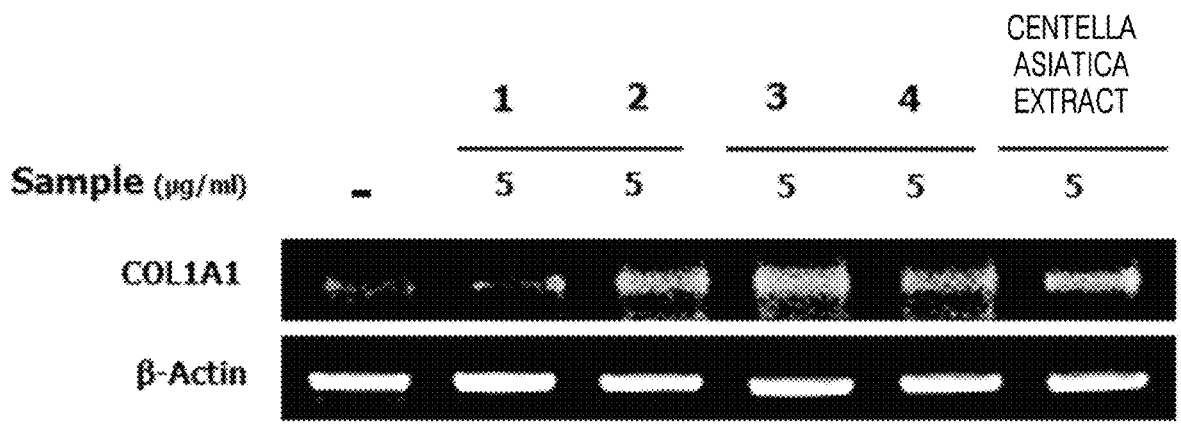
FIG. 5 shows that butanol extracts of an aerial part of *Stellera chamaejasme*, the butanol extracts being extracted in butanols having different concentrations, promote expression of COL1A1 and COL3A1 genes in a fibroblast.

FIG. 5 shows that butanol extracts of an aerial part of *Stellera chamaejasme*, the butanol extracts being extracted in butanols having different concentrations, promote expression of COL1A1 and COL3A1 genes in a fibroblast. In FIG. 5, Samples 1, 2, 3, and 4 respectively represent a 25% butanol extract, a 50% butanol extract, a 75% butanol extract, and a 100% butanol extract.

As shown in FIGS. 4 and 5, it was found that the acetone, methanol, ethanol, and butanol extracts of an aerial part of *Stellera chamaejasme* significantly activates expression of at least one gene selected from the group consisting of COL1A1 and COL3A1, which are collagen synthesis related factors.

TABLE 1

|  | β-actin | COL1A1 | COL3A1 |
| --- | --- | --- | --- |
| Forward primer | SEQ ID NO: 1 | SEQ ID NO: 3 | SEQ ID NO: 5 |
| Reverse primer | SEQ ID NO: 2 | SEQ ID NO: 4 | SEQ ID NO: 6 |

4. Measurement Experiment of Suppression of Collagenase-1 Secretion in Fibroblast that is Senescence-Induced by UV Irradiation The suppressing effects of the ethanol extract of *Stellera chamaejasme* on formation of collagenase-1 (Matrix Metalloproteinase-1, MMP-1) was tested.

First, human fibroblasts were added to each well of 24-well microtiter plate containing DMEM medium containing 2.5% fetal bovine serum such that $1\times10^5$ cells were placed in each well. the human fibroblasts were cultured until a confluency thereof reached 90%. Then, the ethanol extract of *Stellera chamaejasme* dissolved in a serum-free DMEM medium was added thereto at a concentration of 1 μg/mL, 5 μg/mL, and 10 μg/mL in each medium. Then, the cell culture was allowed to continue for 24 hours. Thereafter, irradiation with 15 mJ ultraviolet B (UVB) was performed by using a UV irradiator. Subsequently, the ethanol extract of *Stellera chamaejasme* dissolved in a serum-free DMEM medium was further added thereto at a concentration of 1 μg/mL, 5 μg/mL, and 10 μg/mL in each medium. After 24 hours, the cell culture medium was collected therefrom, which was then centrifuged to thereby obtain a supernatant only.

A level of MMP-1 of the collected supernatant was measured by using ELISA kits: MMP-1 (QIA55, available from Merck&Co., USA). First, the supernatant was added to a 96-well plate, on which a mouse anti-MMP-1 antibody as a primary antibody was uniformly coated. Then, for 2 hours, incubation was performed thereon at room temperature to allow the formation of an antigen-antibody complex. After a lapse of 2 hours, an anti-MMP-1 antibody conjugated to a horseradish peroxidase, as a chromophore, was added to the 96-well plate. Then, for 1 hour, incubation was performed thereon. After a lapse of 1 hour, tetramethylbenzidine (as a chromogenic substrate) was added thereto. Then, for 30 minutes, incubation was performed at room temperature thereon to allow color formation. Subsequently, a terminating buffer was added thereto to stop the reaction. The color of the reaction solution was yellow, and a degree of yellow color varied depending on a degree of the reaction progression. The absorbance of the wells of the yellow-colored 96-well plate was measured at 450/540 nanometers (nm) using a plate reader.

Figure 6:
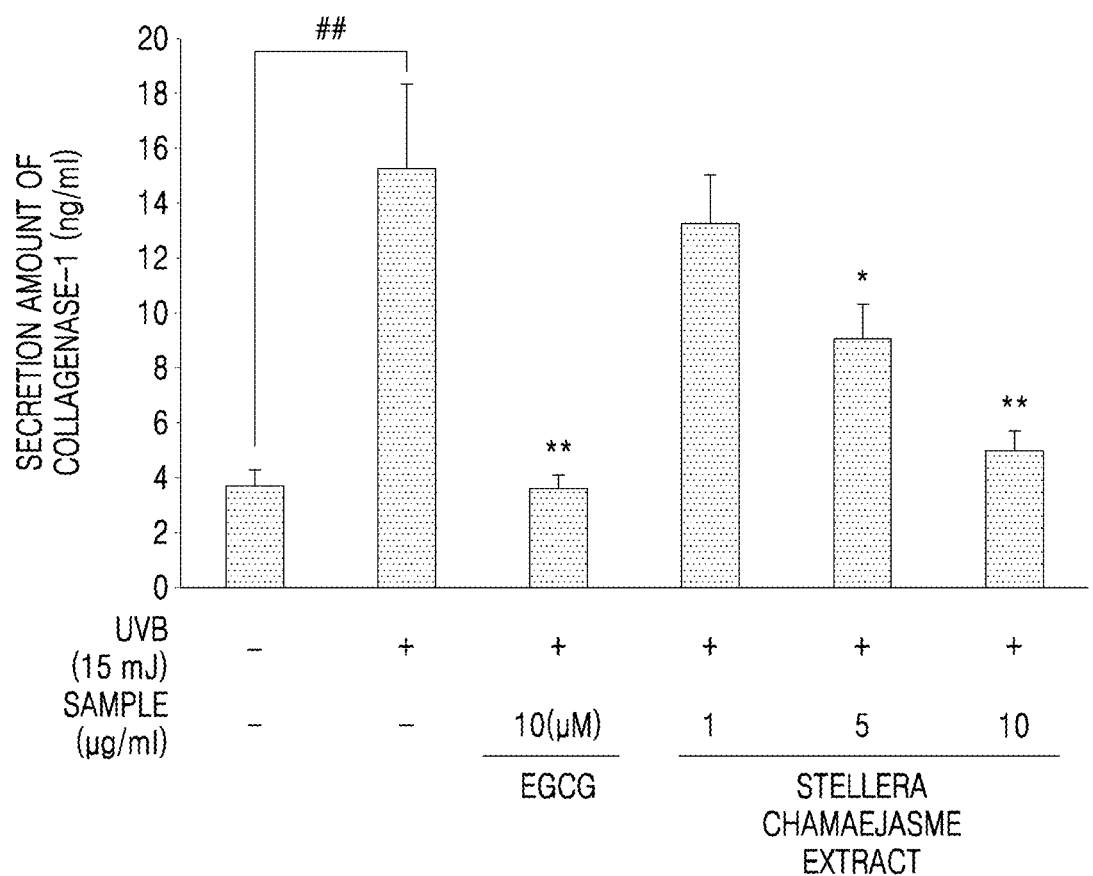
FIG. 6 shows an effect of a presence of an ethanol extract of *Stellera chamaejasme* on an expression level of MMP-1.

FIG. 6 shows the effect of a presence of an ethanol extract of *Stellera chamaejasme* on an expression level of MMP-1. As shown in FIG. 6, it was found that the ethanol extract of *Stellera chamaejasme* has a significant suppressing effect on expression of a MMP-1 gene. As a positive control, epigallocatechin gallate (EGCG) was used.

5. Measurement Experiment of Promotion of Collagen Production in Fibroblast that is Senescence-Induced by UV Irradiation It was tested whether the ethanol extract of *Stellera chamaejasme* promotes expression of Type I procollagen (Type-1 procollagen).

First, human fibroblasts were added to each well of 24-well microtiter plate containing DMEM medium containing 2.5% fetal bovine serum such that $1\times10^5$ cells were placed in each well. the human fibroblasts were cultured until a confluency thereof reached 90%. Then, the ethanol extract of *Stellera chamaejasme* dissolved in a serum-free DMEM medium was added thereto at a concentration of 1 μg/mL, 5 μg/mL, and 10 μg/mL in each medium. Then, the cell culture was allowed to continue for 24 hours. Thereafter, irradiation with 15 mJ UVB was performed by using a UV irradiator. Subsequently, the *Stellera chamaejasme* extract dissolved in a serum-free DMEM medium was further added thereto at a concentration of 1 μg/mL, 5 μg/mL, and 10 μg/mL in each medium. Then, the cell culture was allowed to continue in the same manner. After a lapse of 24 hours, the cell culture medium was collected therefrom, which was then centrifuged to thereby obtain a supernatant only. Subsequently, a level of procollagen Type I C-peptide (PIP) in the obtained supernatant was measured by using a PIP EIA Kit (Cat. #MK101, available from Takara Bio Inc., Japan). PIP is a peptide that is cleaved from procollagen during the process of synthesis of collagen from procollagen in vivo. A level of PIP is in proportion to a level of collagen. Thus, PIP is a peptide that is used as an index for testing a level of collagen in the art.

In detail, a mouse anti-PIP monoclonal antibody conjugated to a horseradish peroxidase (POD) (also referred to as an "antibody-POD conjugate") was added to a 96-well plate, on which a mouse anti-PIP monoclonal antibody was uniformly coated. Subsequently, the cell culture medium and a standard solution were each added to each well, and then the plate was allowed to stand at a temperature of 37° C. for 3 hours. The wells was then washed, and a substrate solution including hydrogen peroxide and tetramethylbenzidine was added to each well. Then, the wells was incubated for 15 minutes. A stop solution was next added to each well so as to stop the reaction. The absorbance of the wells was measured at 450 nm using a plate reader.

Figure 7:
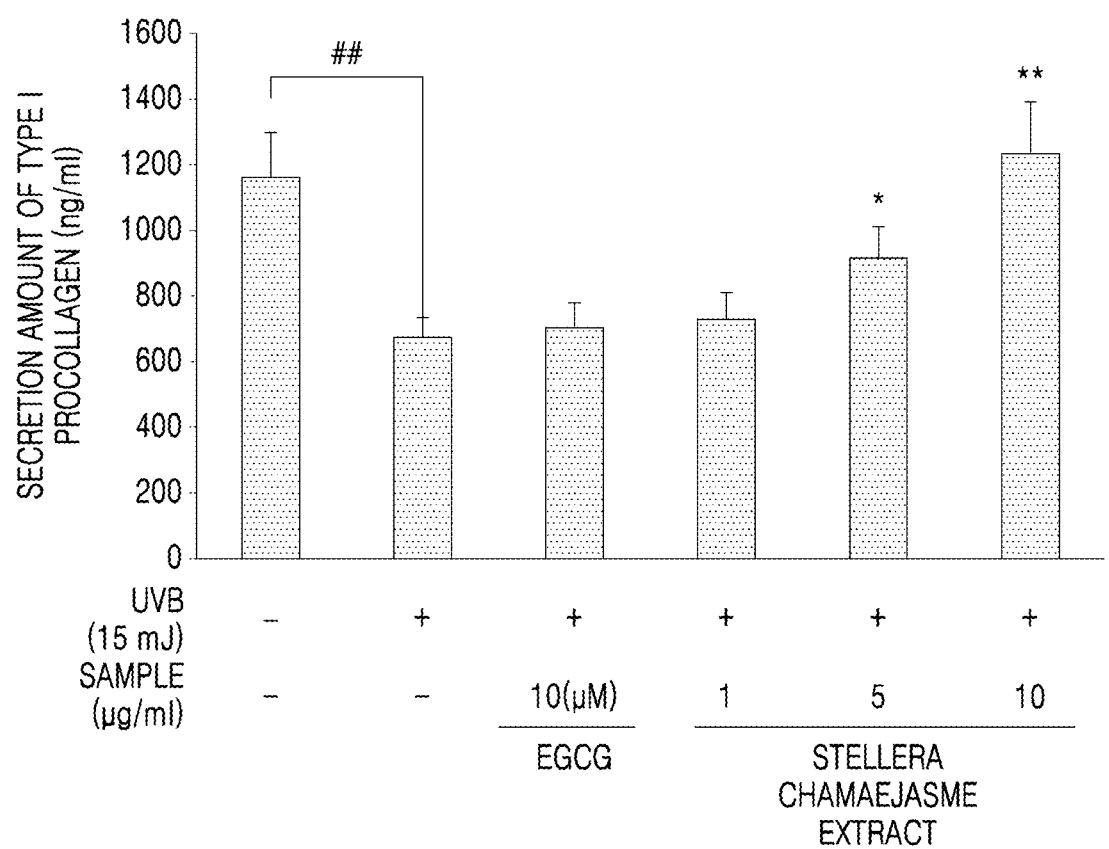
FIG. 7 shows measurement results of a degree of effects of an ethanol extract of *Stellera chamaejasme* on expression of Type I procollagen in a human fibroblast irradiated with UVB.

FIG. 7 shows the measurement results of a degree of effects of an ethanol extract of *Stellera chamaejasme* on expression of Type I procollagen in a human fibroblast irradiated with UVB. As shown in FIG. 7, it was found that the ethanol extract of *Stellera chamaejasme* has a significant promoting effect on expression of Type I procollagen.

6. Improvement of Wound Healing During Animal Experiment

It was tested whether the *Stellera chamaejasme* extract promotes wound healing in an animal experiment.

(1) Laboratory Animals

Sprague-Dawley (SD) rats (male, 7-week-old) were purchased from Koatech, Co., Ltd. A condition of a temperature of 25±1° C., a humidity of 50%±10%, and a photoperiod of 12 hours of light and 12 hours of darkness were maintained by automatic control. In addition, the rats were allowed to freely consume feeds of normal diet and water. All of the laboratory animals were allowed to have one week for adapting to the environment of an animal room, and then used in experiments. The dietary, the dosage, and the method of administration to experimental groups are shown in Table 2.

TABLE 2

| Experimental group | Testing material | Dosage and administration method |
| --- | --- | --- |
| G1 | Vehicle | — |
| G2 | *Centella asiatica* extract | 1%(v/v), once a day |
| G3 | *Centella asiatica* extract | 3%(v/v), once a day |
| G4 | Ethanol extract of *Stellera chamaejasme* | 1%(v/v), once a day |
| G5 | Ethanol extract of *Stellera chamaejasme* | 3%(v/v), once a day |

(2) Wound Induction and Treatment

SD rats were fasted for 24 hours before putting the SD rats under anesthesia, and 100 mL of water were fed to the SD rats. 1 hour prior to wound induction in each of the experimental groups, 100% zoletil was mixed with 100% rompun at a ratio of 1:2 to prepare a mixture. Each of the experimental group was put under anesthesia by an intramuscular injection using the mixture at 0.1 cc/kg. After that, hairs on the dorsal surface of each of the rats were removed by using an electric depilator for all experimental groups. After applying disinfection of 10% povidone-iodine and 70% (v/v) ethanol to the dorsal surface, a full-thickness excisional wound (including the dermis layer) having a square size of 2 cm×2 cm was induced by cutting with sterilized surgical scissors.

(3) Observation of Changes in Wound by Naked Eye

Each of the *Stellera chamaejasme* extract (1% or 3% (v/v)) and the *Centella asiatica* extract (1% or 3% (v/v)), which is known as effective in wound healing, were applied to the wounded skin for two weeks once a day. The *Centella asiatica* extract is the same as those described in Section 2 of Examples 1. The wounded area was photographed at 1, 4, 8, 11, and 15 days after each test material was applied to the wound, and the wounded area was measured and analyzed using ImageJ (NIH, USA).

(4) Histological Examination

On the 14$^{th}$ day after application of each test material, all experimental groups were put under inhalation anesthesia using ether, and a part, to which the test material was administered, was fixed with 10% neutral-buffered formalin solution. For histopathologic examination, the fixed skin tissue was cut one by one with a length of 2 cm×2 cm square with respect to the major axis of the wounded surface so that the wounded surface was examined evenly. The cut tissue was embedded in paraffin according to a general tissue processing method, and a piece of the tissue was formed to a thickness in a range of about 3 μm to 4 μm and attached to a slide glass. The attached pieces were stained with hematoxylin-eosin (H&E), and the stained pieces were examined using an optical microscope (Olympus BX53, Japan). The interpretation of the wounded tissue (e.g., a cut) was score-evaluated according to the evaluation of Nisbet et al. (Tissue Eng Part A. 2010, September; 16 (9): 2833-42) and Barati et al (Diagn Pathol. 2013; 8:120). The criteria for the evaluation are shown in Table 3.

TABLE 3

| Histopatholo-gical parameter | Score | | | |
|---|---|---|---|---|
| | 0 | 1 | 2 | 3 |
| Epithelial-ization | Not progressed | Partially progressed | Completely progressed, but immature or thin | Completely and maturely progressed |

Figure 8:
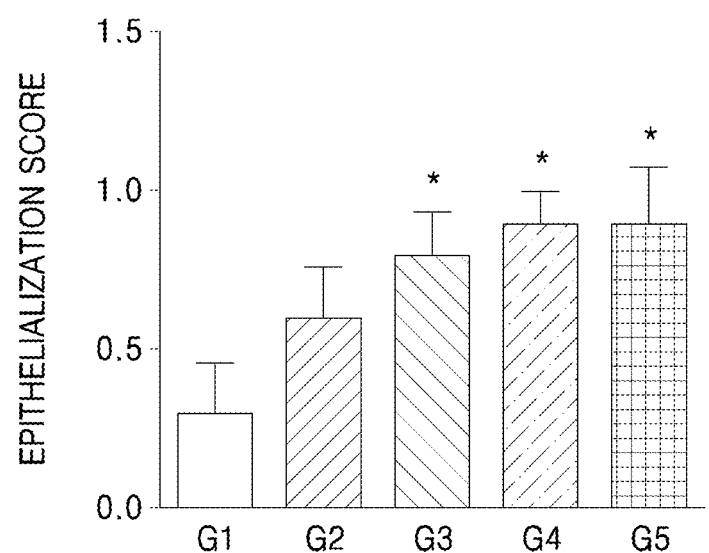
FIG. 8 shows effects of a *Stellera chamaejasme* extract on epithelialization of a rift wound in an animal experiment.

FIG. 8 shows effects of the ethanol extract of *Stellera chamaejasme* on epithelialization of a rift wound in an animal experiment. In FIG. 8, G1, G2, G3, G4, and G5 in the x-axis represent the same experimental groups shown in Table 2, and the scores in the y-axis are measured values based on the epithelialization criteria shown in Table 3.

Figure 9:
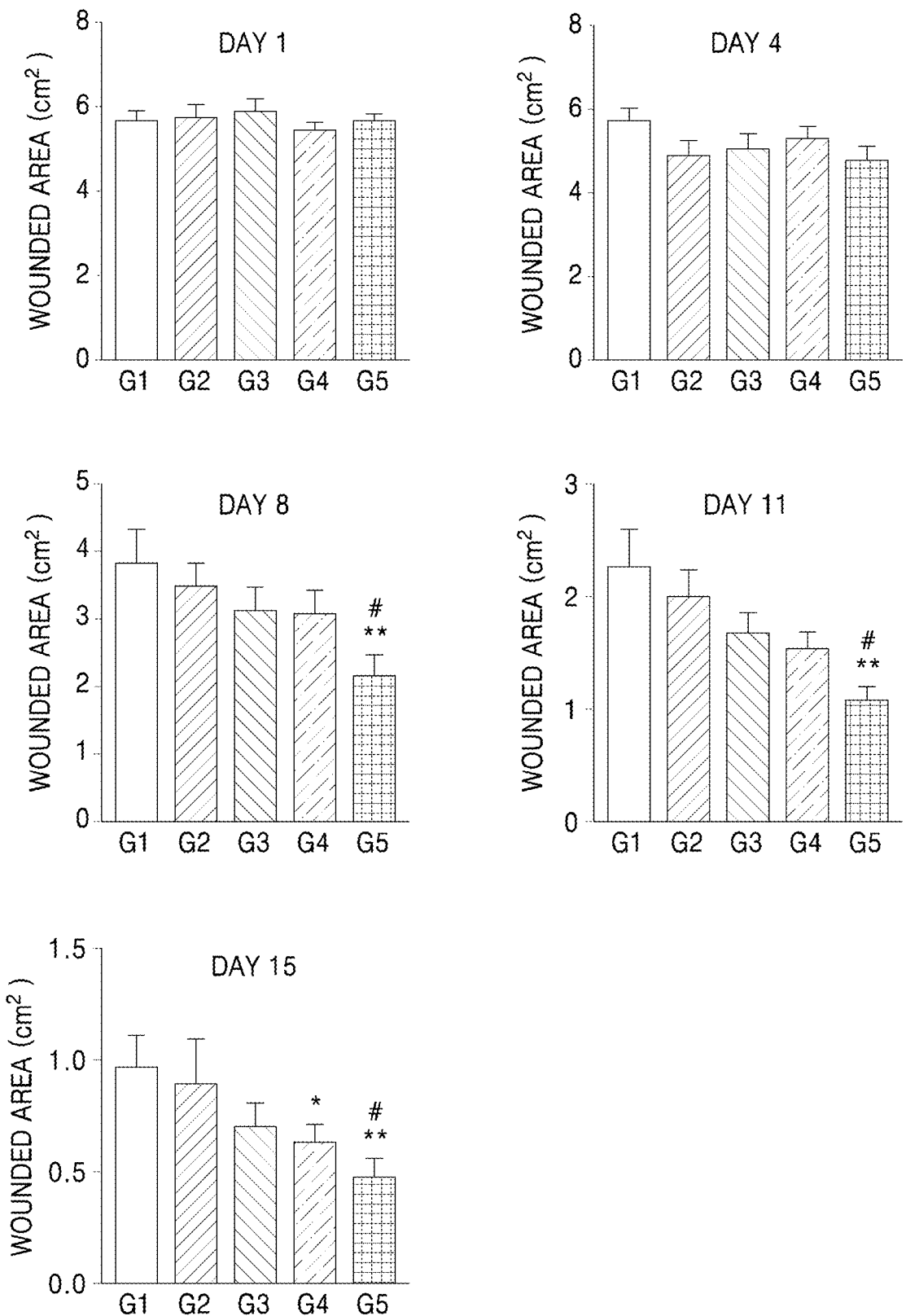
FIG. 9 shows effects of a *Stellera chamaejasme* extract on reduction of wounded area of a rift wound in an animal experiment.

As shown in FIG. 8, the *Stellera chamaejasme* extracts of the present invention shown as G4 and G5 significantly improved epithelialization, as compared with the control group, G1. In FIGS. 8 and 9, * indicates ANOVA by Scheffe's test ($p<0.05$).

FIG. 9 shows effects of the ethanol extracts of *Stellera chamaejasme* on reduction of wounded area of a rift wound in an animal experiment. In FIG. 9, the wounded area represents the results of the measured wounded area at 1, 4, 8, 11, and 15 days after applying *Stellera chamaejasme* extract to the wound. In FIG. 9, G1, G2, G3, G4, and G5 in the x-axis represent the same experimental groups shown in Table 2, and the y-axis represents the wounded area. As shown in FIG. 9, the *Stellera chamaejasme* extracts of the present invention shown as G4 and G5 significantly decreased the wounded area, as compared with the control group, G1.

Figure 10:
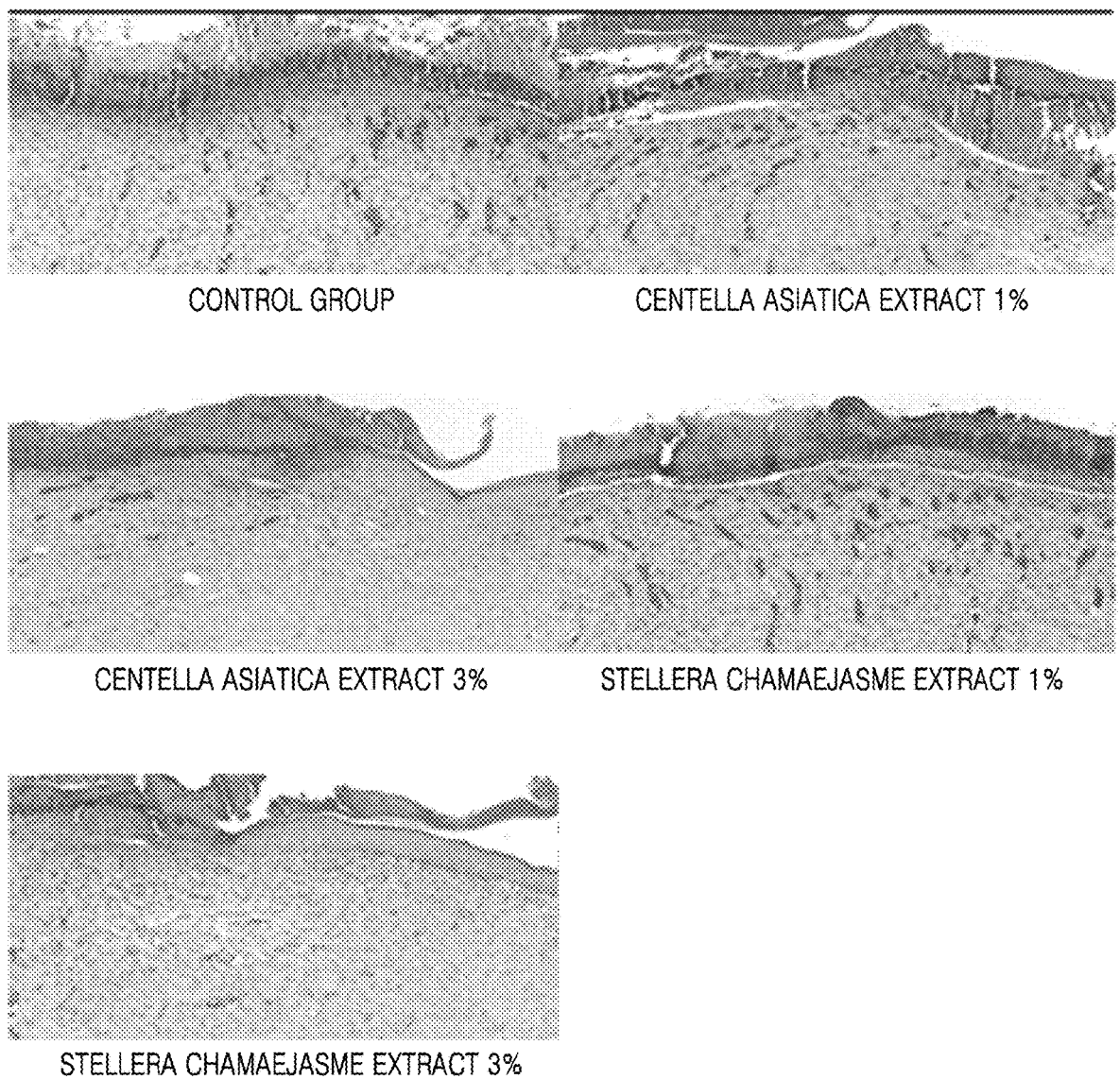
FIG. 10 shows that a *Stellera chamaejasme* extract promotes recovery of a rift wound in an animal experiment, tested by a hematoxylin-eosin (H&E) staining protocol.

FIG. 10 shows that the ethanol extracts of *Stellera chamaejasme* promote recovery of a rift wound in an animal experiment, tested by a hematoxylin-eosin (H&E) staining protocol. As shown in FIG. 10, it was found that the *Stellera chamaejasme* extract of the present invention promotes re-epithelialization of a wound, as compared with the control group. As shown in FIG. 8, when H&E tissue staining is used, two kinds of layers may be found; the upper pink layer is the epidermis and the lower pink layer is the dermis. Upon comparing the control group with the group treated with the sample, it can be seen that the group treated with the sample recovered in light of the thickness and cracking of the epidermis, i.e., the upper layer.

According to the results described above, it was found that a *Stellera chamaejasme* extract promotes re-epithelialization of a rift wound in an animal experiment and significantly promotes recovery of the wound. The above results are based on the use of an ethanol extract of an aerial part of *Stellera chamaejasme*; however, a hexane, ethyl acetate, or butanol fraction of the ethanol extract of an aerial part of *Stellera chamaejasme*; and an acetone, methanol, or butanol extract of an aerial part of *Stellera chamaejasme*, or a hexane, ethyl acetate, or butanol fraction thereof were also found to have similar results.

Further, according to the above described Example, under ultraviolet (UV) irradiation, it was found that a *Stellera chamaejasme* extract reduces expression of MMP-1, and promotes expression of collagen in a human fibroblast. That is, under UV irradiation, the *Stellera chamaejasme* extract reduces expression of collagenase and promotes expression of collagen in a human fibroblast. Thus, the *Stellera chamaejasme* extract may promote elasticity of a tissue containing human fibroblasts, for example, by promoting collagen synthesis in skin. Thus, the *Stellera chamaejasme* extract is effective for improving tissues including human fibroblasts, for example, the *Stellera chamaejasme* extract is effective for skin wrinkle improving or skin anti-aging.

Example 2: Preparation of Stem Extract of *Stellera chamaejasme* and Fraction Thereof In Example 1, a stem extract of *Stellera chamaejasme* and a fraction thereof were prepared from *Stellera chamaejasme*, and effects of the stem extract of *Stellera chamaejasme* and the fraction thereof on wound treatment were tested.

1. Preparation of Stem Extract of *Stellera chamaejasme* and Fraction Thereof (1) Preparation of Stem Extract of *Stellera chamaejasme*

Only a stem of an aerial part of *Stellera chamaejasme* grown in Ulaanbaatar, Mongolia was collected. The collected stem was washed with water and dried. The dried stem of *Stellera chamaejasme* was sliced into, by using a straw cutter, small segments having a size in a range of 2 cm to 3 cm. 100 g of the sliced stem of *Stellera chamaejasme* and IL of ethanol were added to a glass Erlenmeyer flask, and then mixed together. The mixture was extracted while stirring at a rate of 150 rpm at a room temperature of about 20° C. for 48 hours.

Next, the mixture was filtered through a filter paper (Whatman, NO. 2, 8 μm) to thereby obtain a filtrate. The obtained filtrate was concentrated under reduced pressure by using a rotary evaporator (N-1100 available from EYELA). In order to remove the remaining solvent, freeze drying was performed thereon using a freeze dryer (FDCF-12003 available from Operon) for 48 hours, thereby obtaining 3 g of dried stem *Stellera chamaejasme* extract from which the solvent was removed.

(2) Preparation of Fraction of Stem Extract of *Stellera chamaejasme*

3 g of the dried stem *Stellera chamaejasme* extract and 100 mL of water were added to an Erlenmeyer flask and then suspended. The suspension was poured into 250 mL of a separatory funnel, and 100 mL of n-hexane (extra pure grade, 95% or greater) was added thereto, followed by sufficient shaking. Then, the mixture was allowed to stand for 3 hours at room temperature. A hexane layer was only taken from the mixture using a separatory funnel. This process was repeated for three times, and a hexane fraction was obtained and concentrated under reduced pressure by using a rotary evaporator (N-1100 available from EYELA) to thereby obtain a resulting hexane fraction.

Also, in the same manner, ethyl acetate was added to and mixed with the water fraction from which the hexane fraction was removed. Then, the same process was performed thereon to thereby obtain an ethyl acetate fraction.

Also, in the same manner, water-saturated butanol was added to and mixed with the water fraction from which the ethyl acetate fraction was removed. Then, the same process was performed thereon to thereby obtain a butanol fraction.

The extract of *Stellera chamaejasme* and a fraction thereof were dissolved in DMSO at a concentration of 20 mg/mL and used in the following experiment.

2. Increase of Migration of Human Keratinocyte

It was tested whether the stem extract of *Stellera chamaejasme* or a fraction thereof increases migration of a human keratinocyte as follows.

HaCaT human keratinocytes were added to each well of a 24-well microtiter plate containing 1 mL of HyClone DMEM containing 2.5% (v/v) of fetal bovine serum such that $2\times10^5$ cells were placed in each well. Next, the keratinocytes were cultured at a temperature of 37° C. and in 5% $CO_2$ incubator until a confluency thereof reached 80%. A cell monolayer in the medium was "scratch-injured" with a p10 pipette tip.

Subsequently, 200 μl of serum-free DMEM, and the *Stellera chamaejasme* extract or a fraction thereof were added to the scratched cell monolayer at a concentration of 5 μg/mL and 10 μg/mL in each medium. Then, the human keratinocytes were cultured under the same culture conditions for 24 hours. In a negative control, the same amount of DMSO, which was used to dissolve the extract, was treated, and in a positive control, a GW501516 (available from Sigma-Aldrich, USA), i.e., a peroxisome proliferator activated receptor δ (PPARδ) activator, or a *Centella asiatica* extract was used at a given concentration. Thereafter, the cell layer was stained using a crystal violet reagent, to test a degree of recovery of scratch wound. The *Centella asiatica* extract was purchased from Biospectrum (Korea).

Figure 11:
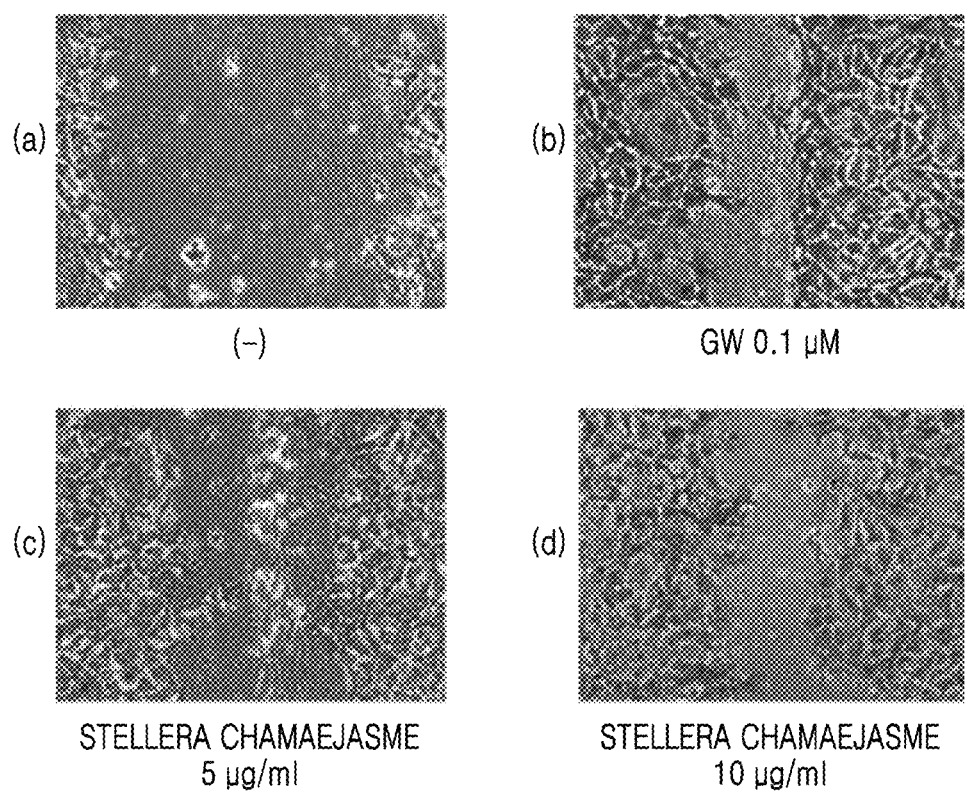
FIG. 11 shows that a stem extract of *Stellera chamaejasme* promotes migration of keratinocyte.

FIG. 11 shows that the stem extract of *Stellera chamaejasme* promotes migration of keratinocyte.

Figure 12:
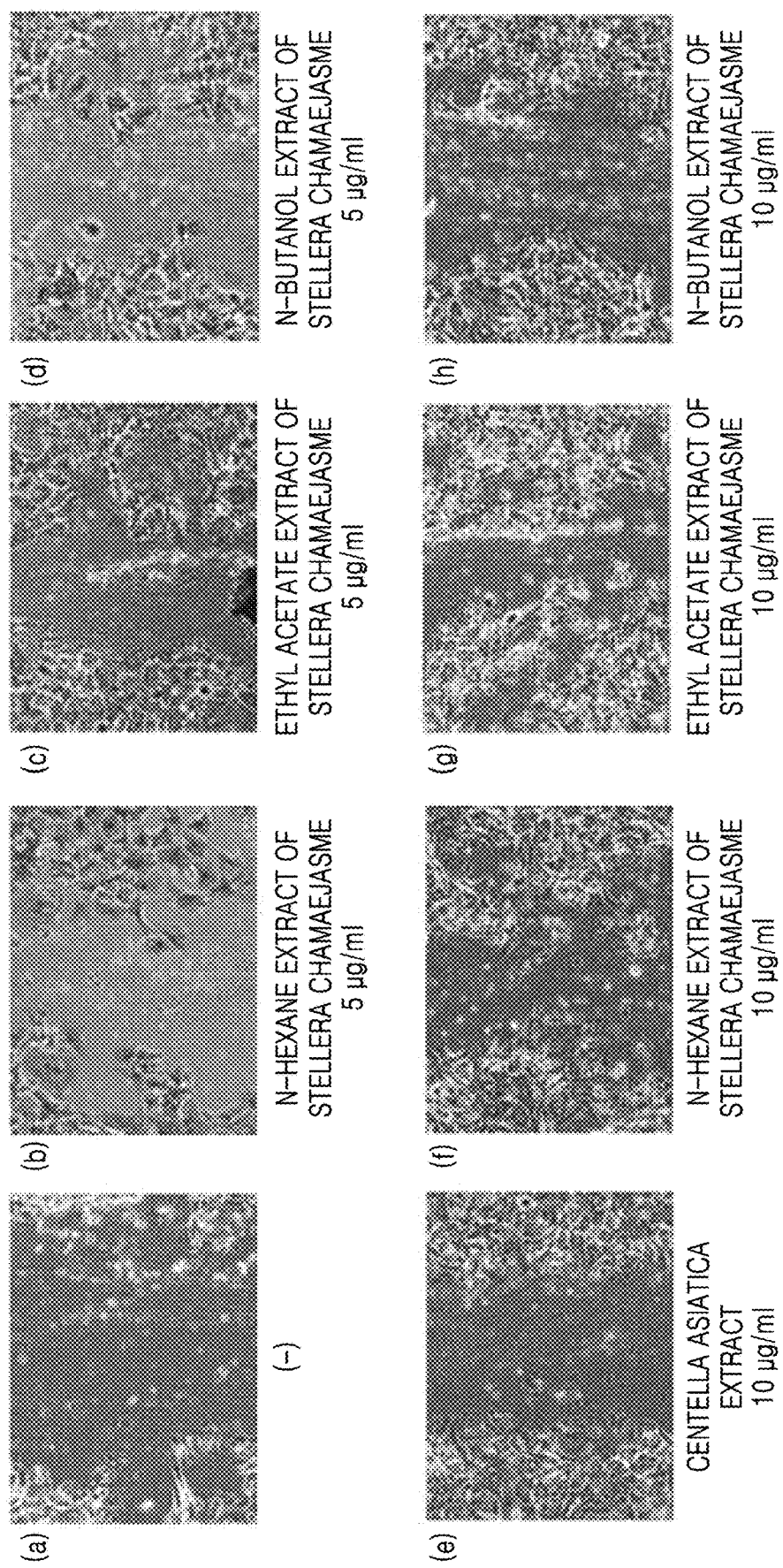
FIG. 12 shows that a fraction of a stem extract of *Stellera chamaejasme* promotes migration of keratinocyte.

FIG. 12 shows that the fraction of a stem extract of *Stellera chamaejasme* promotes migration of keratinocyte.

As shown in FIGS. 11 and 12, in the negative control conditions, the scratch injury of the treated cells remains relatively unhealed after 24 hours of the treatment. On the other hand, in the cells treated with the stem extract of an aerial part of *Stellera chamaejasme* or a fraction thereof, the scratch injury were healed due to proliferation and migration of wound edges, and thus after 24 hours, the scratched area reduced. In FIG. 11, GW represents GW501516.

3. Increase of Expression of COL1A1 and COL3A1 Genes in Fibroblast

It was tested whether the stem extract of *Stellera chamaejasme* or a fraction thereof promotes expression of collagen genes in a human fibroblast.

HDF (available from American Type Culture Collection, USA) were added to each well of a 6-well microtiter plate containing 2 mL of HyClone DMEM containing 2.5% (v/v) of fetal bovine serum such that $2\times10^6$ cells were placed in each well. Next, the human dermal fibroblasts were cultured under the same conditions until a confluency thereof reached 80%.

The stem extract of *Stellera chamaejasme* was added to the cultured cells as such at a concentration of 1 μg/mL, 5 μg/mL, and 10 μg/mL in each medium. The fraction of the stem extract of *Stellera chamaejasme* was added thereto at a concentration of 15 μg/mL and 10 μg/mL in each medium. Then, the cell culture was allowed to continue for 24 hours under the same conditions described above. In a negative control, the same amount of DMSO, which was used to dissolve the extract, was treated, and in a positive control, a *Centella asiatica* extract (available from Biospectrum, Korea) was used. After a lapse of 24 hours, expression of collagen genes was tested by RT-PCR assay. In detail, after a lapse of 24 hours, the total RNAs were collected from the cells using a TRIzol reagent (available from Invitrogen, Carlsbad, Calif., USA), which was then reverse transcripted to perform RT-PCR as follows. First, in order to synthesize cDNAs, the RNAs were reverse transcripted using a reverse transcriptase. The RT-PCR was performed using specific primers shown in Table 1. The relative amount of mRNA expression of each gene was standardized based on an amount of β-actin.

Figure 13:
FIG. 13 shows that a stem extract of *Stellera chamaejasme* promotes expression of COL1A1 and COL3A1 genes in a fibroblast.

FIG. 13 shows that the stem extract of *Stellera chamaejasme* promotes expression of COL1A1 and COL3A1 genes in a fibroblast.

Figure 14:
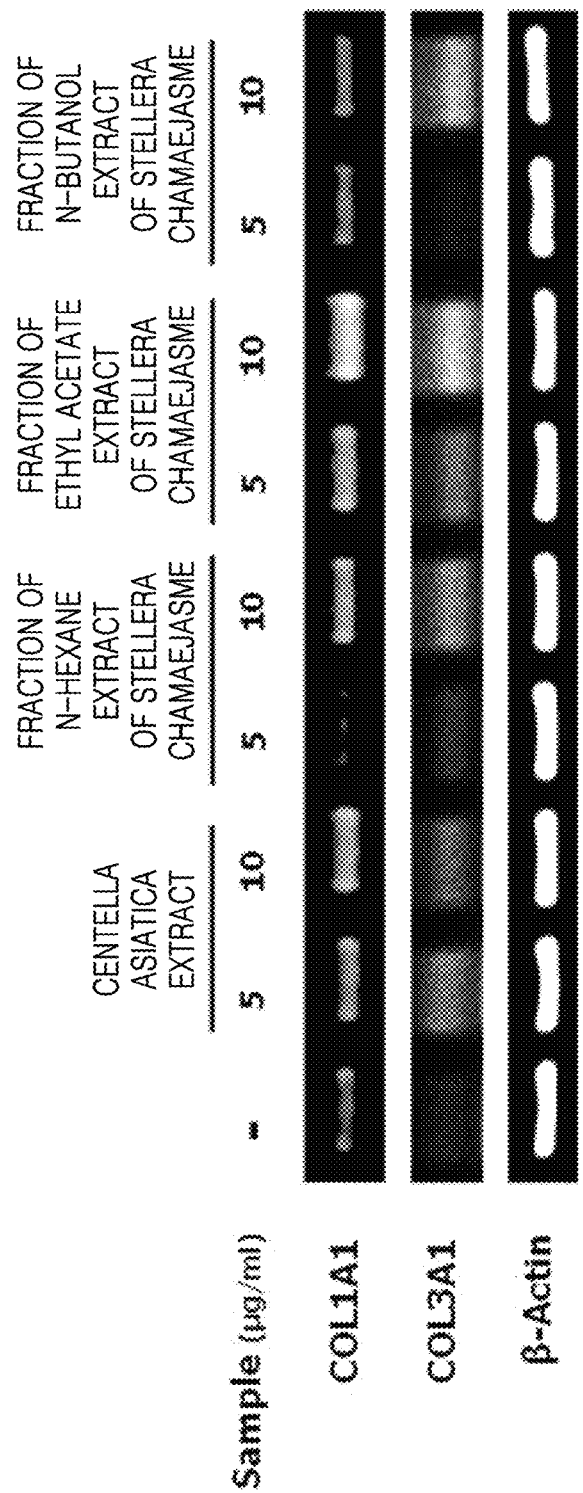
FIG. 14 shows that a fraction of a stem extract of *Stellera chamaejasme* promotes expression of COL1A1 and COL3A1 genes in a fibroblast.

FIG. 14 shows that the fraction of a stem extract of *Stellera chamaejasme* promotes expression of COL1A1 and COL3A1 genes in a fibroblast.

As shown in FIGS. 13 and 14, it was found that the stem extract of *Stellera chamaejasme* or a fraction thereof significantly activates expression of at least one gene selected from the group consisting of COL1A1 and COL3A1, which are collagen synthesis-related factors.

4. Improvement of Wound Healing During Animal Experiment

It was tested whether the stem extract of *Stellera chamaejasme* promotes wound healing in an animal experiment.

(1) Laboratory Animals

SD rats (male, 7-week-old) were purchased from Koatech, Co., Ltd. A condition of a temperature of 25±1° C., a humidity of 50%±+10%, and a photoperiod of 12 hours of light and 12 hours of darkness were maintained by automatic control. In addition, the rats were allowed to freely consume feeds of normal diet and water. All of the laboratory animals were allowed to have one week for adapting to the environment of an animal room, and then used in experiments. The dietary, the dosage, and the method of administration to experimental groups are shown in Table 4.

TABLE 4

Constitution of experimental group, dosage of testing material, and administration method

| Experimental group | Testing material | Dosage and administration method |
|---|---|---|
| G1 | Not progressed | — |
| G2 | Vehicle | — |
| G3 | *Stellera chamaejasme* extract | 3%(v/v), once a day |
| G4 | *Centella asiatica* extract | 3%(v/v), once a day |

(2) Wound Induction and Treatment

SD rats were fasted for 24 hours before putting the SD rats under anesthesia, and 100 mL of water were fed to the SD rats. 1 hour prior to wound induction in each of the experimental groups, 100% zoletil was mixed with 100% rompun at a ratio of 1:2 to prepare a mixture. Each of the experimental group was put under anesthesia by an intramuscular injection using the mixture at 0.1 cc/kg. After that, hairs on the dorsal surface of each of the rats were removed by using an electric depilator for all experimental groups. After applying disinfection of 10% povidone-iodine and 70% ethanol to the dorsal surface, a full-thickness excisional wound (including the dermis layer) having a square size of 2 cm×2 cm was induced by cutting with sterilized surgical scissors.

(3) Observation of Changes in Wound by Naked Eye

Each of the stem extract of *Stellera chamaejasme* (3% (v/v)) and the *Centella asiatica* extract (3% (v/v)), which is known as effective in wound healing, were applied to the wounded skin once a day. The *Centella asiatica* extract is the same as those described in Section 2 of Examples 1. The wounded area was photographed at 1, 4, 8, 11, and 14 days after each test material was applied to the wound, and the wounded area was measured and analyzed using ImageJ (NIH, USA).

(4) Histological Examination

On the 14$^{th}$ day after application of each test material, all experimental groups were put under inhalation anesthesia using ether, and a part, to which the test material was administered, was fixed with 10% neutral-buffered formalin solution. For histopathologic examination, the fixed skin tissue was cut one by one with a length of 2 cm×2 cm square with respect to the longitudinal direction of the wounded surface so that the wounded surface was examined evenly. The cut tissue was embedded in paraffin according to a general tissue processing method, and a piece of the tissue was formed to a thickness in a range of about 3 μm to 4 μm and attached to a slide glass. The attached pieces were stained with hematoxylin-eosin (H&E), and the stained pieces were examined using an optical microscope (Olympus BX53, Japan). The interpretation of the wounded tissue was score-evaluated according to an evaluation method known in the art (Nisbet et al. (Tissue Eng Part A. 2010, September; 16 (9): 2833-42) and Barati et al (Diagn Pathol. 2013; 8:120)). The criteria for the evaluation are shown in Table 5. The interpretation results are shown in Table 6.

As shown in Table 6, it can be seen that the stem extract of *Stellera chamaejasme* has significant effects on formation of fibrous tissue, angiogenesis, and epithelialization.

Figure 15:
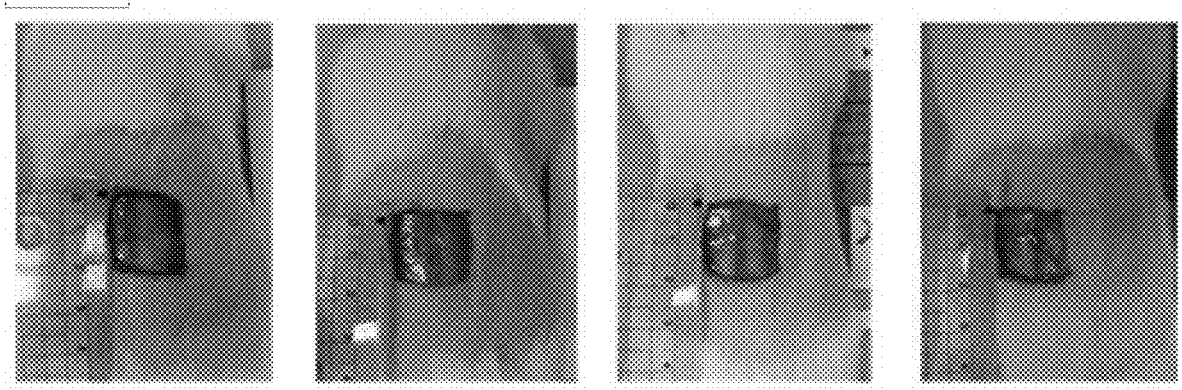
FIG. 15 shows clinical test results where a stem extract of *Stellera chamaejasme* promotes recovery of a rift wound in an animal experiment.
Figure 15:
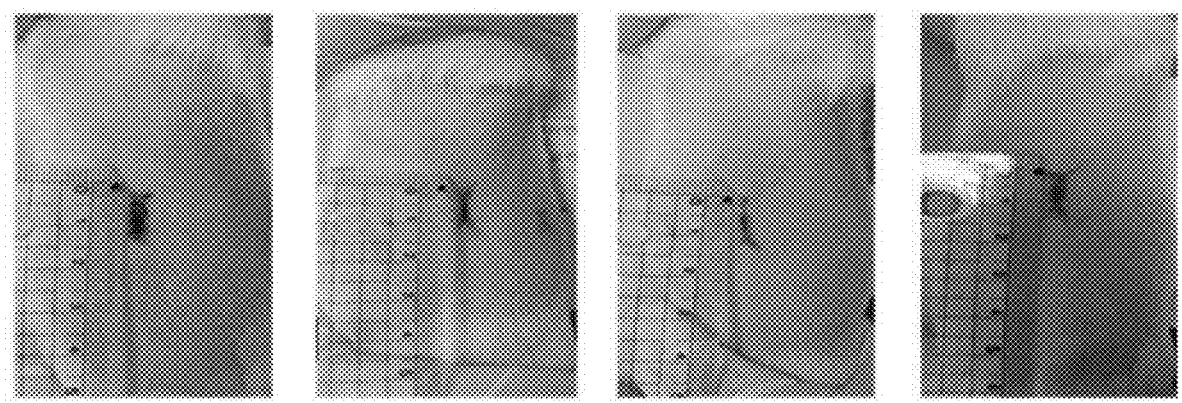

FIG. 15 shows clinical test results where the stem extract of *Stellera chamaejasme* promotes recovery of a rift wound in an animal experiment. FIG. 16 shows quantitative test results where the stem extract of *Stellera chamaejasme* promotes recovery of a rift wound in an animal experiment. As shown in FIGS. 15 and 16, it was found that the *Stellera chamaejasme* extract promotes re-epithelialization of a wounded part, and significantly facilitates recovery of a dehiscenced wound.

TABLE 5

| Histopathological parameter | Score | | | |
|---|---|---|---|---|
| | 0 | 1 | 2 | 3 |
| Inflammation | Not progressed | Mild | Moderate | Marked |
| Formation of fibrous tissue | Not occurred or at least level of fibroblasts were formed | Few fibroblasts | A number of fibroblasts | Majority of fibroblasts |
| Angiogenesis | Not progressed | 5 or less blood vessels per high power field (HPF) | 6 to 10 blood vessels per HPF | More than 10 blood vessels per HPF |
| Epithelialization | Not progressed | Partially progressed | Focal defective | Completed |

TABLE 6

| Experimental group | Histopathological parameter | | | |
|---|---|---|---|---|
| | Inflammation | Formation of fibrous tissue | Angiogenesis | Epithelialization |
| G1 | 2.6 | 2.4 | 2.3 | 1.6 |
| G2 | 2.5 | 2.4 | 2.2 | 1.7 |
| G3 | 2.4 | 2.6 | 2.5 | 1.8* |
| G4 | 2.3* | 2.7* | 2.5 | 1.6 |

*indicates $P < 0.05$, which represents statistical significance with G1.

Preparation Example 1: Preparation of a Pharmaceutical Preparation

1. Preparation of Soft Capsule

A soft capsule was prepared by mixing 150 mg of an ethanol stem extract of *Stellera chamaejasme* or a fraction thereof, 2 mg of palm oil, 8 mg of hydrogenated palm oil, 4 mg of yellow wax, and 6 mg of lecithin and filling the soft capsule up to 400 mg per capsule according to a conventional method.

2. Preparation of Tablet 150 mg of an ethanol stem extract of *Stellera chamaejasme* or a fraction thereof, 100 mg of glucose, 50 mg of red ginseng extract, 96 mg of starch, and 4 mg of magnesium stearate were mixed, and 40 mg of 30% ethanol was added thereto to form granules. The granules were then dried at a temperature of 60° C., and tableted by using a tablet machine.

3. Preparation of Granules 150 mg of an ethanol stem extract of *Stellera chamaejasme* or a fraction thereof, 100 mg of glucose, 50 mg of red ginseng extract, and 600 mg of starch were mixed, and 100 mg of 30% ethanol was added thereto to form granules. The granules were then dried at a temperature of 60° C., and then filled in a pack. The final weight of the content was 1 g.

Preparation Example 2: Preparation of a Cosmetic Composition

In Preparation Example 2, an ethanol stem extract of *Stellera chamaejasme* was used.

1. Preparation of Moisturizers (Skin Lotion)

TABLE 7

| Compounding component | Amount (wt %) |
|---|---|
| *Stellera chamaejasme* extract or a fraction thereof | 0.1 |
| Glycerin | 3.0 |
| Butylene glycol | 2.0 |
| Propylene glycol | 2.0 |
| Carboxy vinyl polymer | 0.1 |
| PEG-12 nonylphenyl ether | 0.2 |
| Polysorbate 80 | 0.4 |
| Ethanol | 10.0 |
| Triethanolamine | 0.1 |
| Preservatives, pigments, perfumes | Proper amount |
| Distilled water | The remaining part |

2. Preparation of Nutrition Lotion (Milk Lotion)

TABLE 8

| Compounding component | Amount (wt %) |
|---|---|
| *Stellera chamaejasme* extract or a fraction thereof | 0.1 |
| Glycerin | 3.0 |
| Butylene glycol | 3.0 |
| Propylene glycol | 3.0 |
| Carboxy vinyl polymer | 0.1 |
| Wax | 4.0 |
| Polysorbate 60 | 1.5 |
| Caprylic/capric triglyceride | 5.0 |
| Squalane | 5.0 |
| Sorbitan sesquioleate | 1.5 |
| Liquid paraffin | 0.5 |
| Cetearyl alcohol | 1.0 |
| Triethanolamine | 0.2 |
| Preservatives, pigments, perfumes | Proper amount |
| Distilled water | The remaining part |

3. Preparation of Nutrition Cream

TABLE 9

| Compounding component | Amount (wt %) |
|---|---|
| *Stellera chamaejasme* extract or a fraction thereof | 0.1 |
| Glycerin | 3.0 |
| Butylene glycol | 3.0 |
| Liquid paraffin | 7.0 |
| Betaglucan | 7.0 |
| Carbomer | 0.1 |
| Caprylic/capric triglyceride | 3.0 |
| Squalane | 5.0 |
| Cetearyl glucoside | 1.5 |
| Sorbitan stearate | 0.4 |
| Polysorbate 60 | 1.2 |
| Triethanolamine | 0.1 |
| Preservatives, pigments, perfumes | Proper amount |
| Distilled water | The remaining part |

4. Preparation of Massage Cream

TABLE 10

| Compounding component | Amount (wt %) |
|---|---|
| *Stellera chamaejasme* extract or a fraction thereof | 0.1 |
| Glycerin | 8.0 |
| Butylene glycol | 4.0 |
| Liquid paraffin | 45.0 |
| Betaglucan | 7.0 |
| Carbomer | 0.1 |
| Caprylic/capric triglyceride | 3.0 |
| Wax | 4.0 |
| Cetearyl glucoside | 1.5 |
| Sorbitan sesquioleate | 0.9 |
| Vaseline | 3.0 |
| Parafin | 1.5 |
| Preservatives, pigments, perfumes | Proper amount |
| Distilled water | The remaining part |

5. Preparation of Pack

TABLE 11

| Compounding component | Amount (wt %) |
|---|---|
| *Stellera chamaejasme* extract or a fraction thereof | 0.1 |
| Glycerin | 4.0 |
| Polyvinyl alcohol | 15.0 |
| Hyaluronic acid extract | 5.0 |
| Betaglucan | 7.0 |
| Allantoin | 0.1 |
| Nonyl phenyl ether | 0.4 |
| Polysorbate 60 | 1.2 |
| Ethanol preservative | 6.0 proper amount |
| Preservatives, pigments, perfumes | Proper amount |
| Distilled water | The remaining part |

6. Preparation of Ointment

TABLE 12

| Compounding component | Amount (wt %) |
|---|---|
| *Stellera chamaejasme* extract or a fraction thereof | 0.1 |
| Glycerin | 8.0 |
| Butylene glycol | 4.0 |
| Liquid paraffin | 15.0 |
| Betaglucan | 7.0 |
| Carbomer | 0.1 |
| Caprylic/capric triglyceride | 3.0 |
| Squalane | 1.0 |
| Cetearyl glucoside | 1.5 |
| Sorbitan stearate | 0.4 |
| Cetearyl alcohol | 1.0 |
| Wax | 4.0 |
| Preservatives, pigments, perfumes | Proper amount |
| Distilled water | The remaining part |

The invention claimed is:

1. A method of improving skin wrinkles, comprising applying to the wrinkled skin a cosmetic composition, wherein the cosmetic composition is for improving skin wrinkles, said cosmetic composition comprises a fraction of a *Stellera chamaejasme* extract as an active ingredient,
   wherein the *Stellera chamaejasme* extract is extracted from an aerial part of *Stellera chamaejasme*,
   wherein the *Stellera chamaejasme* extract is extracted in water, acetone, a $C_1$-$C_6$ alcohol, or a combination thereof,
   wherein said improving skin wrinkles is by promoting expression of a collagen gene in a cell, and
   wherein the fraction is a hexane fraction, a butanol fraction, or a combination thereof,
      wherein the hexane fraction and the butanol fraction are obtained by suspending the *Stellera chamaejasme* extract in water and then subsequently fractionating a suspension by using hexane and butanol.

2. The method of claim 1, wherein the *Stellera chamaejasme* extract is extracted in 75% (v/v) to 100% (v/v) ethanol, 75% (v/v) to 100% (v/v) methanol, 75% (v/v) to 100% (v/v) butanol, or a combination thereof.

3. The method of claim 1, wherein an amount of the *Stellera chamaejasme* extract or the fraction thereof is in a range of 0.001 percent by weight (wt %) to 80 wt %, based on an amount of the cosmetic composition.

4. The method of claim 1, the cosmetic composition further comprises a cosmetically acceptable excipient or carrier.

* * * * *

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: forward primer

<400> SEQUENCE: 1
agccatgtac gtagccatcc                                             20

<210> SEQ ID NO 2
<211> LENGTH: 20
<212> TYPE: DNA
<213> ORGANISM: Artificial Sequence
<220> FEATURE:
<223> OTHER INFORMATION: reverse primer

<400> SEQUENCE: 2
ctctcagctg tggtggtgaa                                             20

<210> SEQ ID NO 3
<211> LENGTH: 20
<212> TYPE: DNA
<213> ORGANISM: Artificial Sequence
<220> FEATURE:
<223> OTHER INFORMATION: forward primer

<400> SEQUENCE: 3
tgagcggacg ctaaccccct                                             20

<210> SEQ ID NO 4
<211> LENGTH: 20
<212> TYPE: DNA
<213> ORGANISM: Artificial Sequence
<220> FEATURE:
<223> OTHER INFORMATION: reverse primer

<400> SEQUENCE: 4
cagacgggac agcactcgcc                                             20

<210> SEQ ID NO 5
<211> LENGTH: 20
<212> TYPE: DNA
<213> ORGANISM: Artificial Sequence
<220> FEATURE:
<223> OTHER INFORMATION: forward primer

<400> SEQUENCE: 5
agccatgtac gtagccatcc                                             20

<210> SEQ ID NO 6
<211> LENGTH: 20
<212> TYPE: DNA
<213> ORGANISM: Artificial Sequence
<220> FEATURE:
<223> OTHER INFORMATION: reverse primer

<400> SEQUENCE: 6
tacggggcaa aaccgccagc                                             20